US 8,348,956 B2

(12) United States Patent
Rabiner

(10) Patent No.: US 8,348,956 B2
(45) Date of Patent: *Jan. 8, 2013

(54) APPARATUS AND METHODS FOR REINFORCING BONE

(75) Inventor: Robert A. Rabiner, Tiverton, RI (US)

(73) Assignee: IlluminOss Medical, Inc., East Providence, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 12/886,288

(22) Filed: Sep. 20, 2010

(65) Prior Publication Data
US 2011/0009871 A1    Jan. 13, 2011

Related U.S. Application Data

(62) Division of application No. 11/789,906, filed on Apr. 26, 2007, now Pat. No. 7,811,290.

(60) Provisional application No. 60/795,626, filed on Apr. 26, 2006, provisional application No. 60/858,202, filed on Nov. 10, 2006, provisional application No. 60/880,646, filed on Jan. 16, 2007.

(51) Int. Cl.
*A61B 17/56* (2006.01)
(52) U.S. Cl. .......................................... 606/94
(58) Field of Classification Search ............. 606/92–95, 606/108, 192, 65–67; 623/23.14, 23.19, 623/23.2, 23.48, 23.62
See application file for complete search history.

(56) References Cited

U.S. PATENT DOCUMENTS

| 4,280,233 A | 7/1981 | Raab |
| 4,294,251 A | 10/1981 | Greenwald et al. |
| 4,313,434 A | 2/1982 | Segal |
| 4,341,691 A | 7/1982 | Anuta |
| 4,369,772 A | 1/1983 | Miller |
| 4,422,719 A | 12/1983 | Orcutt |
| 4,433,898 A | 2/1984 | Nasiri |
| 4,462,394 A | 7/1984 | Jacobs |
| 4,466,435 A | 8/1984 | Murray |
| 4,686,973 A | 8/1987 | Frisch |
| 4,697,584 A | 10/1987 | Haynes |
| 4,735,625 A | 4/1988 | Davidson |
| 4,870,953 A | 10/1989 | DonMichael et al. |

(Continued)

FOREIGN PATENT DOCUMENTS

NL    9001858    3/1992

(Continued)

OTHER PUBLICATIONS

Office Action in U.S. Appl. No. 11/964,370 mailed Dec. 9, 2010.

(Continued)

*Primary Examiner* — Eduardo C Robert
*Assistant Examiner* — David Comstock
(74) *Attorney, Agent, or Firm* — Greenberg Traurig, LLP; David J. Dykeman; Danielle T. Abramson

(57) ABSTRACT

Apparatuses and methods for reinforcing weakened or fractured bone are disclosed. An apparatus for delivering a bone reinforcing mixture to a bone includes a tube having a proximal end, a distal end, and a longitudinal axis therebetween, wherein the tube has at least one inner lumen capable of allowing a bone reinforcing mixture to pass through, and a bone fitting portion having an opening for accepting the tube, an insertion portion for insertion into the bone, and at least one relief valve.

24 Claims, 9 Drawing Sheets

U.S. PATENT DOCUMENTS

| | | | |
|---|---|---|---|
| 4,888,024 A | 12/1989 | Powlan |
| 4,904,391 A | 2/1990 | Freeman |
| 4,961,424 A | 10/1990 | Kubota et al. |
| 4,963,151 A | 10/1990 | Ducheyne et al. |
| 4,969,888 A | 11/1990 | Scholten et al. |
| 5,030,093 A | 7/1991 | Mitnick |
| 5,049,157 A | 9/1991 | Mittelmeier et al. |
| 5,092,899 A | 3/1992 | Forte |
| 5,102,413 A | 4/1992 | Poddar |
| 5,108,404 A | 4/1992 | Scholten et al. |
| 5,112,333 A | 5/1992 | Fixel |
| 5,295,733 A | 3/1994 | LeBegue |
| 5,303,718 A | 4/1994 | Krajicek |
| 5,316,550 A | 5/1994 | Forte |
| 5,336,699 A | 8/1994 | Cooke et al. |
| 5,372,598 A | 12/1994 | Luhr et al. |
| 5,391,144 A | 2/1995 | Sakurai et al. |
| 5,415,654 A | 5/1995 | Daikuzono |
| 5,423,850 A | 6/1995 | Berger |
| 5,432,876 A | 7/1995 | Appeldorn et al. |
| 5,443,468 A | 8/1995 | Johnson |
| 5,462,552 A | 10/1995 | Kiester |
| 5,480,400 A | 1/1996 | Berger |
| 5,548,676 A | 8/1996 | Savage, Jr. |
| 5,554,111 A | 9/1996 | Morrey et al. |
| 5,556,429 A | 9/1996 | Felt |
| 5,658,310 A | 8/1997 | Berger |
| 5,658,963 A | 8/1997 | Qian et al. |
| 5,705,181 A | 1/1998 | Cooper et al. |
| 5,707,374 A | 1/1998 | Schmidt |
| 5,795,353 A | 8/1998 | Felt |
| 5,824,087 A | 10/1998 | Aspden et al. |
| 5,827,289 A | 10/1998 | Reiley et al. |
| 5,888,220 A | 3/1999 | Felt et al. |
| 5,897,557 A | 4/1999 | Chin et al. |
| 5,908,433 A | 6/1999 | Eager et al. |
| 5,972,015 A | 10/1999 | Scribner et al. |
| 5,980,075 A | 11/1999 | Sheaffer |
| 5,980,253 A | 11/1999 | Oxman et al. |
| 5,987,199 A | 11/1999 | Zarian et al. |
| 5,989,230 A | 11/1999 | Frassica |
| 6,019,761 A | 2/2000 | Gustilo |
| 6,019,774 A | 2/2000 | Weiss et al. |
| 6,033,411 A | 3/2000 | Preissman |
| 6,039,762 A | 3/2000 | McKay |
| 6,042,380 A | 3/2000 | De Rowe |
| 6,059,789 A | 5/2000 | Dinger et al. |
| 6,066,154 A | 5/2000 | Reiley et al. |
| 6,079,868 A | 6/2000 | Rydell |
| 6,110,176 A | 8/2000 | Shapira |
| 6,121,341 A | 9/2000 | Sawhney et al. |
| 6,127,597 A | 10/2000 | Beyar et al. |
| 6,140,452 A | 10/2000 | Felt et al. |
| 6,179,852 B1 | 1/2001 | Strickland et al. |
| 6,195,477 B1 | 2/2001 | Denuto et al. |
| 6,200,134 B1 | 3/2001 | Kovac et al. |
| 6,217,581 B1 | 4/2001 | Tolson |
| 6,224,630 B1 | 5/2001 | Bao et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,280,456 B1 | 8/2001 | Scribner et al. |
| 6,290,382 B1 | 9/2001 | Bourn et al. |
| 6,299,597 B1 | 10/2001 | Buscemi et al. |
| 6,306,177 B1 | 10/2001 | Felt et al. |
| 6,319,255 B1 | 11/2001 | Grundei et al. |
| 6,336,914 B1 | 1/2002 | Gillespie, III |
| 6,336,930 B1 | 1/2002 | Stalcup et al. |
| 6,358,252 B1 | 3/2002 | Shapira |
| 6,387,098 B1 | 5/2002 | Cole et al. |
| 6,395,007 B1 | 5/2002 | Bhatnagar et al. |
| 6,416,737 B1 | 7/2002 | Manolagas et al. |
| 6,423,083 B2 | 7/2002 | Reiley et al. |
| 6,425,923 B1 | 7/2002 | Stalcup et al. |
| 6,440,444 B2 | 8/2002 | Boyce et al. |
| 6,443,988 B2 | 9/2002 | Felt et al. |
| 6,447,514 B1 | 9/2002 | Stalcup et al. |
| 6,458,375 B1 | 10/2002 | Gertzman et al. |
| 6,478,751 B1 | 11/2002 | Krueger et al. |
| 6,485,512 B1 | 11/2002 | Cheng |
| 6,494,883 B1 | 12/2002 | Ferree |
| 6,524,251 B2 | 2/2003 | Rabiner et al. |
| 6,551,337 B1 | 4/2003 | Rabiner et al. |
| 6,565,528 B1 | 5/2003 | Mueller |
| 6,579,277 B1 | 6/2003 | Rabiner et al. |
| 6,579,279 B1 | 6/2003 | Rabiner et al. |
| 6,620,185 B1 | 9/2003 | Harvie et al. |
| 6,623,505 B2 | 9/2003 | Scribner et al. |
| 6,648,881 B2 | 11/2003 | KenKnight et al. |
| 6,652,547 B2 | 11/2003 | Rabiner et al. |
| 6,652,587 B2 | 11/2003 | Felt et al. |
| 6,660,013 B2 | 12/2003 | Rabiner et al. |
| 6,679,873 B2 | 1/2004 | Rabiner et al. |
| 6,695,781 B2 | 2/2004 | Rabiner et al. |
| 6,695,782 B2 | 2/2004 | Rabiner et al. |
| 6,696,073 B2 | 2/2004 | Boyce et al. |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,048 B1 | 5/2004 | Hare et al. |
| 6,733,451 B2 | 5/2004 | Rabiner et al. |
| 6,733,513 B2 | 5/2004 | Boyle et al. |
| 6,740,093 B2 | 5/2004 | Hochschuler et al. |
| 6,755,862 B2 | 6/2004 | Keynan |
| 6,802,835 B2 | 10/2004 | Rabiner et al. |
| 6,818,018 B1 | 11/2004 | Sawhney |
| 6,852,095 B1 | 2/2005 | Ray |
| 6,866,678 B2 | 3/2005 | Shenderova et al. |
| 6,869,442 B2 | 3/2005 | Cheng |
| 6,875,212 B2 | 4/2005 | Shaolian et al. |
| 6,885,246 B2 | 4/2005 | Tsutsui et al. |
| 6,887,246 B2 | 5/2005 | Bhatnagar et al. |
| 6,887,275 B2 | 5/2005 | Carchidi et al. |
| 6,899,713 B2 | 5/2005 | Shaolian et al. |
| 6,899,719 B2 | 5/2005 | Reiley et al. |
| 6,932,843 B2 | 8/2005 | Smith et al. |
| 6,964,667 B2 | 11/2005 | Shaolian et al. |
| 6,979,341 B2 | 12/2005 | Scribner et al. |
| 6,981,981 B2 | 1/2006 | Reiley et al. |
| 7,001,431 B2 | 2/2006 | Bao et al. |
| 7,008,433 B2 | 3/2006 | Voellmicke et al. |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,427,295 B2 | 9/2008 | Ellman et al. |
| 7,547,319 B2 | 6/2009 | Segal et al. |
| 7,628,800 B2 | 12/2009 | Sherman et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,766,965 B2 | 8/2010 | Bao et al. |
| 7,771,476 B2 | 8/2010 | Justis et al. |
| 7,806,900 B2 | 10/2010 | Rabiner |
| 7,811,284 B2 | 10/2010 | Rabiner |
| 7,811,290 B2 | 10/2010 | Rabiner |
| 7,842,040 B2 | 11/2010 | Rabiner et al. |
| 7,850,711 B1 * | 12/2010 | Stone et al. ................ 606/232 |
| 7,879,041 B2 | 2/2011 | Rabiner et al. |
| 7,912,539 B2 | 3/2011 | Doty et al. |
| 7,947,015 B2 | 5/2011 | Herweck et al. |
| 8,034,071 B2 | 10/2011 | Scribner et al. |
| 2001/0011174 A1 | 8/2001 | Reiley et al. |

| | | | | | | |
|---|---|---|---|---|---|---|
| 2001/0044626 A1 | 11/2001 | Reiley et al. | | 2009/0112196 A1 | 4/2009 | Rabiner et al. |
| 2002/0156482 A1 | 10/2002 | Scribner et al. | | 2009/0171265 A1 | 7/2009 | Doty et al. |
| 2002/0198526 A1 | 12/2002 | Shaolian et al. | | 2009/0171358 A1 | 7/2009 | Chang et al. |
| 2003/0028210 A1 | 2/2003 | Boyle et al. | | 2009/0177204 A1 | 7/2009 | Colleran et al. |
| 2003/0105469 A1 | 6/2003 | Karmon | | 2009/0187192 A1 | 7/2009 | Rabiner et al. |
| 2003/0114914 A1 | 6/2003 | Cheng | | 2009/0216232 A1 | 8/2009 | Buford, III et al. |
| 2003/0199850 A1 | 10/2003 | Chavez et al. | | 2010/0256641 A1 | 10/2010 | Rabiner et al. |
| 2003/0229372 A1 | 12/2003 | Reiley et al. | | 2010/0262069 A1 | 10/2010 | Rabiner et al. |
| 2004/0006341 A1 | 1/2004 | Shaolian et al. | | 2010/0262188 A1 | 10/2010 | Rabiner et al. |
| 2004/0034434 A1 | 2/2004 | Evans et al. | | 2010/0265733 A1 | 10/2010 | O'Leary et al. |
| 2004/0059333 A1 | 3/2004 | Carl et al. | | 2010/0318087 A1 | 12/2010 | Scribner et al. |
| 2004/0059417 A1 | 3/2004 | Smith et al. | | 2010/0331850 A1 | 12/2010 | Rabiner |
| 2004/0092948 A1 | 5/2004 | Stevens et al. | | 2011/0004213 A1 | 1/2011 | Rabiner et al. |
| 2004/0098015 A1 | 5/2004 | Weikel et al. | | 2011/0046746 A1 | 2/2011 | Rabiner et al. |
| 2004/0117025 A1 | 6/2004 | Reindel | | 2011/0098713 A1 | 4/2011 | Rabiner et al. |
| 2004/0133280 A1 | 7/2004 | Trieu | | 2011/0118740 A1 | 5/2011 | Rabiner et al. |
| 2004/0167625 A1 | 8/2004 | Beyar et al. | | 2011/0166306 A1 | 7/2011 | Stansbury et al. |
| 2004/0225296 A1 | 11/2004 | Reiss et al. | | 2011/0313356 A1 | 12/2011 | Rabiner et al. |
| 2004/0230309 A1 | 11/2004 | Di Mauro et al. | | | | |
| 2004/0247641 A1 | 12/2004 | Felt et al. | | | | |

FOREIGN PATENT DOCUMENTS

| | | |
|---|---|---|
| WO | WO 03/047472 | 6/2003 |
| WO | WO 2004/058045 | 7/2004 |
| WO | WO 2004/073563 | 9/2004 |
| WO | WO 2004/112661 | 12/2004 |
| WO | WO 2005/112804 | 12/2005 |
| WO | WO 2006/016807 | 2/2006 |
| WO | WO 2007/059259 | 5/2007 |
| WO | WO 2007/127255 | 11/2007 |
| WO | WO 2007/127260 | 11/2007 |
| WO | WO 2008/063265 | 5/2008 |
| WO | WO 2009/059090 | 5/2009 |
| WO | WO 2009/082688 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/071567 | 6/2011 |
| WO | WO 2011/162910 | 12/2011 |

| | | |
|---|---|---|
| 2005/0010231 A1 | 1/2005 | Myers |
| 2005/0043733 A1 | 2/2005 | Eisermann et al. |
| 2005/0043808 A1 | 2/2005 | Felt et al. |
| 2005/0090901 A1 | 4/2005 | Studer |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0234453 A1 | 10/2005 | Shaolian et al. |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0036253 A1 | 2/2006 | Leroux et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0155296 A1 | 7/2006 | Richter |
| 2006/0173464 A1 | 8/2006 | Ellman et al. |
| 2006/0183811 A1 | 8/2006 | Melikechi et al. |
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0118143 A1 | 5/2007 | Ralph et al. |
| 2007/0123877 A1 | 5/2007 | Goldin et al. |
| 2007/0161991 A1 | 7/2007 | Altarac et al. |
| 2007/0198023 A1 | 8/2007 | Sand et al. |
| 2007/0225705 A1 | 9/2007 | Osario et al. |
| 2007/0255287 A1 | 11/2007 | Rabiner |
| 2008/0015500 A1 | 1/2008 | Herweck et al. |
| 2008/0039854 A1 | 2/2008 | Rabiner |
| 2008/0080205 A1 | 4/2008 | Forrester et al. |
| 2008/0103505 A1 | 5/2008 | Fransen |
| 2008/0125784 A1 | 5/2008 | Rabiner et al. |
| 2008/0154368 A1 | 6/2008 | Justis |
| 2008/0188858 A1 | 8/2008 | Luzzi et al. |
| 2008/0234820 A1 | 9/2008 | Felt et al. |
| 2008/0269750 A1 | 10/2008 | Justin |
| 2009/0018524 A1 | 1/2009 | Greenhalgh et al. |
| 2009/0048629 A1 | 2/2009 | Rabiner |
| 2009/0054900 A1 | 2/2009 | Rabiner et al. |

OTHER PUBLICATIONS

International Search Report based on PCT/US10/56219 dated Jan. 20, 2011.

Jovanovic et al., "Fixion Nails for Humeral Fractures, Injury", Int. J. Care Injured, vol. 35, Issue 11, pp. 1140-1142, Nov. 2004.

Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.

Waris et al., "Bioabsorbable Miniplating Versus Metallic Fixation for Metacarpal Fractures", Clinical Orthopaedics and Related Research, No. 410, pp. 310-319, May 2003.

Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.

International Search Report based on PCT/US07/20402 dated Apr. 1, 2008.

International Search Report based on PCT/US07/10050 dated Apr. 17, 2008.

International Search Report based on PCT/US07/10038 dated Aug. 27, 2008.

International Search Report based on PCT/US08/81929 dated Jan. 12, 2009.

International Search Report based on PCT/US08/81924 dated Feb. 9, 2009.

International Search Report based on PCT/US08/87630 dated Feb. 24, 2009.

International Search Report based on PCT/US10/30275 dated Aug. 11, 2010.

Office Action in U.S. Appl. No. 11/789,906 mailed Apr. 29, 2009.
Office Action in U.S. Appl. No. 11/789,906 mailed Mar. 11, 2010.
Office Action in U.S. Appl. No. 11/789,906 mailed Apr. 30, 2010.
Office Action in U.S. Appl. No. 11/789,907 mailed May 11, 2010.
Office Action in U.S. Appl. No. 11/903,123 mailed Jul. 1, 2010.
Office Action in U.S. Appl. No. 12/262,411 mailed Sep. 1, 2010.

International Search Report based on PCT/US10/46003 dated May 24, 2011.
Final Office Action in U.S. Appl. No. 11/964,370 mailed Apr. 28, 2011.
PCT International Search Report based on PCT/US11/66871 dated May 1, 2012.
USPTO Office Action in U.S. Appl. No. 12/875,460 mailed Mar. 8, 2012.
USPTO Office Action in U.S. Appl. No. 11/964,370 mailed Mar. 16, 2012.
USPTO Office Action in U.S. Appl. No. 12/858,924 mailed Apr. 4, 2012.
USPTO Office Action in U.S. Appl. No. 12/756,014 mailed May 11, 2012.
PCT International Search Report based on PCT/US11/38389 dated Sep. 22, 2011.
USPTO Office Action in U.S. Appl. No. 11/964,370 mailed Sep. 23, 2011.
USPTO Office Action in U.S. Appl. No. 12/858,924 mailed Oct. 24, 2011.
USPTO Office Action in U.S. Appl. No. 12/755,784 mailed Dec. 23, 2011.

* cited by examiner

APPARATUS AND METHODS FOR REINFORCING BONE

RELATED APPLICATIONS

This application is a divisional of U.S. application Ser. No. 11/789,906, filed on Apr. 26, 2007, which claims the benefit of U.S. Provisional Application Ser. No. 60/795,626, filed on Apr. 26, 2006, U.S. Provisional Application Ser. No. 60/858,202, filed Nov. 10, 2006, and U.S. Provisional Application Ser. No. 60/880,646, filed Jan. 16, 2007, and the entirety of all these applications are hereby incorporated herein by reference for the teachings therein.

FIELD

The embodiments disclosed herein relate to bone strengthening and reinforcing, and more particularly to apparatus and methods for reinforcing a weakened or fractured bone.

BACKGROUND

Bone is a living tissue and plays a structural role in the body. Bone consists of repeating Harvesian systems (concentric layers of lamellae deposited around a central canal containing blood vessels and nerves). The central canal is also known as the medullary cavity and is filled with bone marrow. Within the shaft of a long bone, many of these Harvesian systems are bundled together in parallel, forming a kind of bone called compact bone, which is optimized to handle compressive and bending forces. In some bones, such as the metacarpals, the bones themselves are hollow and contain little, if any, marrow. Near the ends of the bones, where the stresses become more complex, the Harvesian systems splay out and branch to form a meshwork of cancellous or spongy bone. Compact bone and cancellous bone differ in density, or how tightly the tissue is packed together.

The structure of bone is similar to reinforced concrete that is used to make a building or a bridge. When the building or bridge is first assembled, an initial frame that contains long steel rods is put in place. Cement is then poured around these steel rods. The rods and the cement form a tight union, producing a structure that is strong and resilient enough to withstand some rocking motion while maintaining strength. Without the steel rods, the cement would be brittle and fracture with only minor movement. Without the cement, the steel rods would have inadequate support and would bend. The same organization is true of bone. The steel rods that support the building are collagen rods in bone. The cement that surrounds and supports the rods is formed by minerals (including calcium and phosphorus) from the blood that crystallize and surround the collagen rods. These minerals give the bones strength while the collagen rods provide resiliency.

Genetic or developmental irregularities, trauma, chronic stress, tumors, and disease can result in pathologies of bones. Some bone diseases that weaken the bones include, but are not limited to, osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, and scoliosis. Weakened bones are more susceptible to fracture, and treatment to prevent bone fractures becomes important. Severe fractures, such as those that are open, multiple, or to the hip or back, are treated in a hospital. Surgery may be necessary when a fracture is open, severe, or has resulted in severe injury to the surrounding tissues. Severe fractures may require internal devices, such as screws, rods, or plates, to hold the bone in place or replace lost bone during the healing process.

In many cases where the bone has fractured, a bone cement mixture, or a bone void filler, is added into the bone to repair and strengthen the bone. Prior art bone cement mixtures are typically two part (powder and liquid), require a catalyst, and are exothermic. Injection devices similar to a household caulking gun are used to inject bone cement into bone. A typical bone cement injection device has a pistol-shaped body, which supports a cartridge containing bone cement where the injection device is usually a high pressure delivery source. More specifically, a trigger actuates a spring-loaded or screw ram, which forces a volume of bone cement in a viscous condition through a suitable nozzle and into the interior of a bone targeted for treatment. The amount of bone cement mixture injected is a function of the amount of space within the bone structure and the ability to reach the open areas in the bone. In some cases the presence of bone marrow restricts the amount of bone cement mixture that can be used, therefore before a bone cement mixture can be added into the bone for repair, the bone marrow must be removed from the area.

In thermal characterization tests of polymethylmethacrylate (PMMA) bone cement performed according to the ASTM Standard Specification for Acrylic Bone Cement, time and temperature profiles of bone cement were observed to be sensitive to the thickness of the cement patty and the mold material. Due to the heat transfer from the cement to the surrounding mold, such tests might underestimate the exothermic temperature of bone cement. That is, the mold material and geometry may influence the values of the parameters measured.

Bone cements may be difficult to work with and cause complications. Leakage of bone cements can result in soft tissue damage as well as nerve root pain and compression. Other complications associated with the use of bone cements for vertebroplasty and kyphoplasty procedures may include pulmonary embolism, respiratory and cardiac failure, abdominal intrusions, ileus, and death.

Prior art techniques for adding a bone cement mixture to repair or strengthen bone are described in U.S. Pat. No. 4,969,888 entitled "Surgical Protocol for Fixation of Osteoporotic Bone Using Inflatable Device," U.S. Pat. No. 5,108,404 entitled "Surgical Protocol for Fixation of Osteoporotic Bone Using Inflatable Device," U.S. Pat. No. 5,824,087 entitled "Bone Regeneration," U.S. Pat. No. 6,241,734 entitled "Systems and Methods for Placing Materials Into Bone," U.S. Pat. No. 6,395,007 entitled "Apparatus and Method for Fixation of Osteoporotic Bone," U.S. Pat. No. 6,425,923 entitled "Contourable Polymer Filled Implant," U.S. Pat. No. 6,887,246 entitled "Apparatus and Method for Fixation of Osteoporotic Bone," U.S. Pat. No. 6,875,212 entitled "Cureable media for implantable medical device," U.S. Pat. No. 6,964,667 entitled "Formed in place fixation system with thermal acceleration," U.S. Publication No. 2004/0225296 entitled "Devices and methods using an expandable body with internal restraint for compressing cancellous bone," and U.S. Publication No. 2005/0142315 entitled "Liquid perfluoropolymers and medical applications incorporating same."

The prior art injection devices are typically invasive and have difficulty quickly terminating the flow of cement should the cavity fill before the spring-actuated load cycle is completed. Conventional cement injection devices also have difficulty adjusting or controlling the injection volume or injection rate in real time in reaction to cancellous bone volume and density conditions encountered inside the bone.

Thus, there is a need in the art for apparatuses and methods for delivering reinforcing materials into a bone using minimally invasive techniques, with ease of use, greater rate and volume control and a faster response time.

SUMMARY

Systems and methods for reinforcing weakened or fractured bones are disclosed herein. According to aspects illustrated herein, there is provided an apparatus for delivering a bone reinforcing mixture to a bone including a tube having a proximal end, a distal end, and a longitudinal axis therebetween, wherein the tube has at least one inner lumen capable of allowing a bone reinforcing mixture to pass through; and a bone fitting portion having an opening for accepting the tube, an insertion portion for insertion into the bone, and at least one relief valve.

According to aspects illustrated herein, there is provided a system for reinforcing a bone including a tube having a proximal end, a distal end, and a longitudinal axis therebetween, wherein the tube has at least one inner lumen for allowing a bone reinforcing mixture to pass therethrough; and a light source providing light to at least one second inner lumen and to assist in hardening the bone reinforcing mixture.

According to aspects illustrated herein, there is provided a method for reinforcing a bone including penetrating the bone at a site adjacent to a weakened or fractured area of the bone to gain access to an interior of the bone; forming a bone void in the interior of the bone having a distal edge and a proximal edge; inserting a bone fitting portion at the penetration site, the bone fitting portion having an opening, an insertion portion for insertion into the bone, and at least one relief valve; positioning a catheter having a proximal end, a distal end, and a longitudinal axis therebetween through the opening of the bone fitting portion so the distal end of the catheter is within the bone void; infusing a bone reinforcing mixture through at least one inner lumen of the catheter into the bone void; and removing the catheter from the bone fitting portion.

Various embodiments provide certain advantages. Not all embodiments of the invention share the same advantages and those that do may not share them under all circumstances. Further features and advantages of the embodiments, as well as the structure of various embodiments are described in detail below with reference to the accompanying drawings.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Apparatuses and methods for the controlled delivery of reinforcing materials to weakened or fractured bones are disclosed herein. Apparatuses and methods disclosed herein may be performed in a sterile environment. Reinforcing materials include, but are not limited to, bone reinforcing mixtures (such as bone cement mixtures, bone void fillers, epoxies, glues and similar adhesives), orthopedic wires, stainless-steel rods, metal pins, and other similar devices. At least some of the main components of an apparatus for delivering reinforcing materials to weakened or fractured bones are shown in the embodiment depicted in FIG. 1. An apparatus 20 may be used for the repair of bones that have weakened or fractured due to any of the bone diseases including, but not limited to osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, scoliosis, and other similar diseases.

Figure 1:
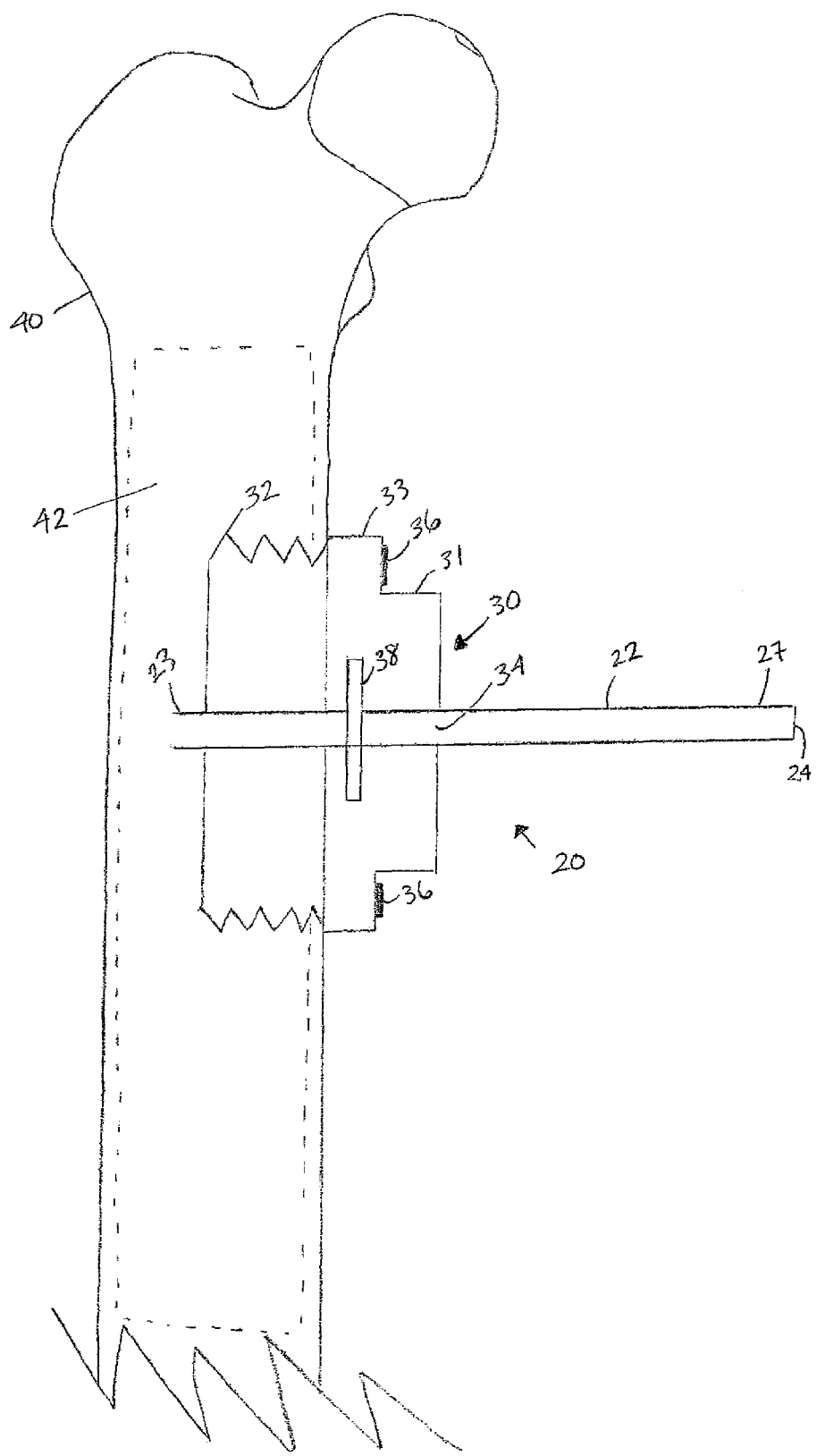
FIG. 1 is a view of an apparatus for delivering a bone reinforcing material of the presently disclosed embodiments.

Referring to FIG. 1, the apparatus 20 may be used for delivering reinforcing materials to a bone void 42 that has been prepared inside a bone 40 using, for example, the disclosed techniques. FIG. 1 shows the weakened or fractured bone 40 as a femur. Those skilled in the art will recognize that the disclosed apparatus and methods can be used for delivering reinforcing materials to other bones, such as the tibia, fibula, humerus, ulna radius, metatarsals, metacarpals, phalanx, phalanges, ribs, spine, vertebrae, clavicle and other bones and still be within the scope and spirit of the disclosed embodiments. The apparatus 20 includes an elongated flexible tube 22 having at least one lumen, capable of receiving a fluid from both ends, which extends through a flexible bone fitting portion 30 that has been screwed into the bone 40 via a screw-thread portion 32. In an embodiment, the elongated flexible tube 22 is a thin catheter. In an embodiment, the elongated flexible tube 22 is a balloon catheter.

Figure 2:
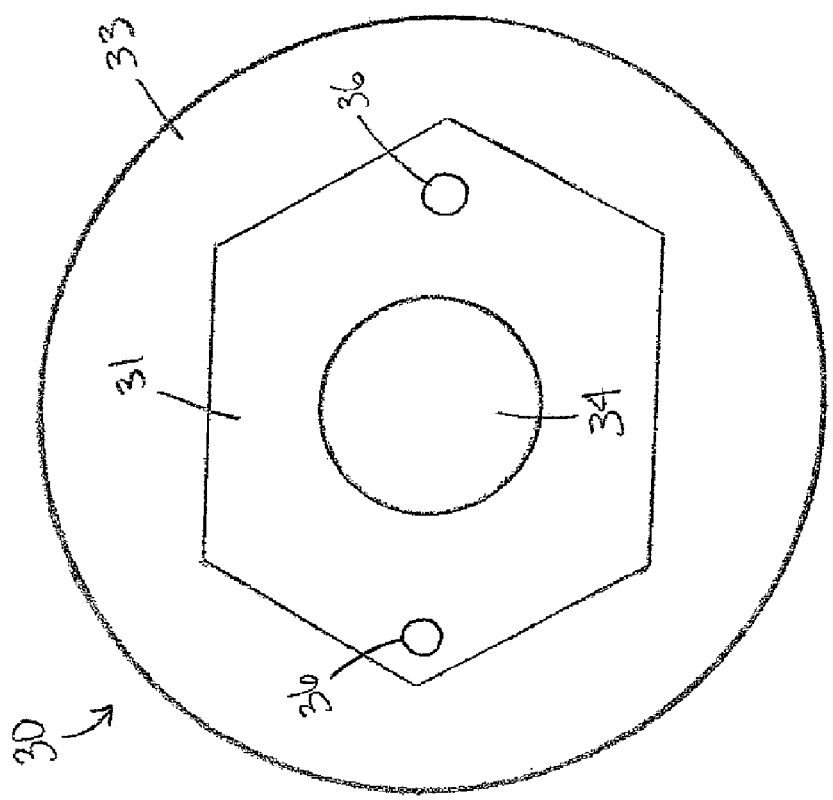
FIG. 2 shows an expanded view of an illustrative embodiment of a flexible bone fitting portion of an apparatus for delivering a bone reinforcing material.

FIG. 2 shows an embodiment of the bone fitting portion 30 which includes a stop plate 33 that rests on the bone 40 when threaded in position and limits the insertion of the bone fitting portion 30 into the bone 40; a grip portion 31 for easy threading into the bone 40; at least one pressure relief valve 36 for relieving any pressure buildup in the bone void 42 during the infusion of a bone reinforcing mixture; and an opening or central hole 34 for insertion of the catheter 22. An O-ring 38, shown in FIG. 1, allows the flexible tube 22 to move freely in the central hole 34 so that the flexible tube 22 may be moved in orientation once inside the bone void 42. For example, the O-ring 38 allows the flexible tube 22 to move from the furthest point in the bone void 42 backwards towards the introduction point. The flexible orientation of the bone fitting portion 30 allows for easy adjustment of the location of the delivery of a bone reinforcing mixture and ensures that directionality of the delivery of the bone reinforcing mixture. The at least one pressure relief valve 36 serves a number of purposes, including, but not limited to, controlling the pressure build-up created during the infusion of the bone reinforcing mixture, egression of air that may be trapped within the lumen of the bone 40 during the insertion of the bone reinforcing mixture, and a means of controlling the amount of bone reinforcing mixture delivered to the bone void 42.

The function of the pressure relief valve may be accomplished using a variety of structures. For example, in an embodiment (not shown), the bone fitting portion may include a weep hole where a small hole allows air to escape but inhibits more viscous materials from escaping through the hole. In an embodiment (not shown), the bone fitting portion may include a vent hole with a tube, such as a catheter, attached thereto. This arrangement allows the air and the glue to bubble out and the operator may discern when the cavity is substantially filled by visually inspecting the catheter tube and seeing whether or not there are bubbles in the fluid. In addition, the catheter tube may be moved around within the bone void so that the catheter can reach different locations. For example, if there is an air pocket in the bone void and the glue is too viscous to allow the air bubble to move to the vent hole, an operator can move the catheter to tap into the air pocket, thereby allowing the air to escape through the vent hole via the catheter.

In an embodiment (not shown), the relief valve may be a dome-like attachment that allows materials to pass through the fitting while catching excess material and/or air. While some embodiments include a structure, for example those described above, to allow for excess air or materials to exit the bone void, such a structure is not required and not all embodiments described herein include a valve or relief structure.

The flexible bone fitting portion includes a stop plate that limits the insertion of the flexible bone fitting portion into the bone; a grip portion for threading the flexible bone fitting portion into the bone; and an O-ring that allows the flexible tube to move in the flexible bone fitting portion. The flexible bone fitting portion may include a plurality of holes that run through the bone fitting portion for accepting a reinforcing material selected from the group consisting of orthopedic wires, stainless steel rods and metal pins.

The bone fitting portion may be a device that assists an operator in inserting instruments and/or materials into a bone void. For example, the bone fitting portion is similar to a cannula or trocar having a central opening for the insertion of instruments and/or materials and a valve for controlling the exit of materials and/or air. In an embodiment (not shown), the bone fitting portion is a grease gun fitting and holds a valve in place while allowing instruments and/or materials to be passed through the fitting. In an embodiment (not shown), the bone fitting portion is a press fitting that may be inserted into a pre-drilled hole in the bone. In an embodiment (not shown) the bone fitting portion may employ an expandable mollybolt, such as is described in U.S. Pat. No. 5,462,552, which is hereby incorporated by reference in its entirety, wherein the device expands to fit the opening in the bone.

In addition, the bone fitting portion may be an integral part of the instrument being inserted into the bone. In an embodiment (not shown), a cylindrically shaped stopper slidably surrounds the catheter, such that when the catheter is inserted into a hole in the bone, the stopper is also inserted into the hole in the bone, thereby substantially blocking the hole surrounding the catheter but still allowing the catheter to be slid into, out of and around the bone void. In an embodiment (not shown), the catheter may be inserted into the bone via a press or force fit.

An operator may take care not to insert the bone fitting portion or equivalent structure too far into the bone, else the inserted portion may be glued in place in the bone. In an embodiment, the bone fitting portion may be made from an adhesion-resistant material, such as polytetrafluoroethylene (PTFE), to prevent adhesion with the glue both when the glue is being inserted through the opening in the bone fitting portion and when the glue fills the bone void and may contact other parts of the bone fitting portion in or near the bone void.

Figure 3:
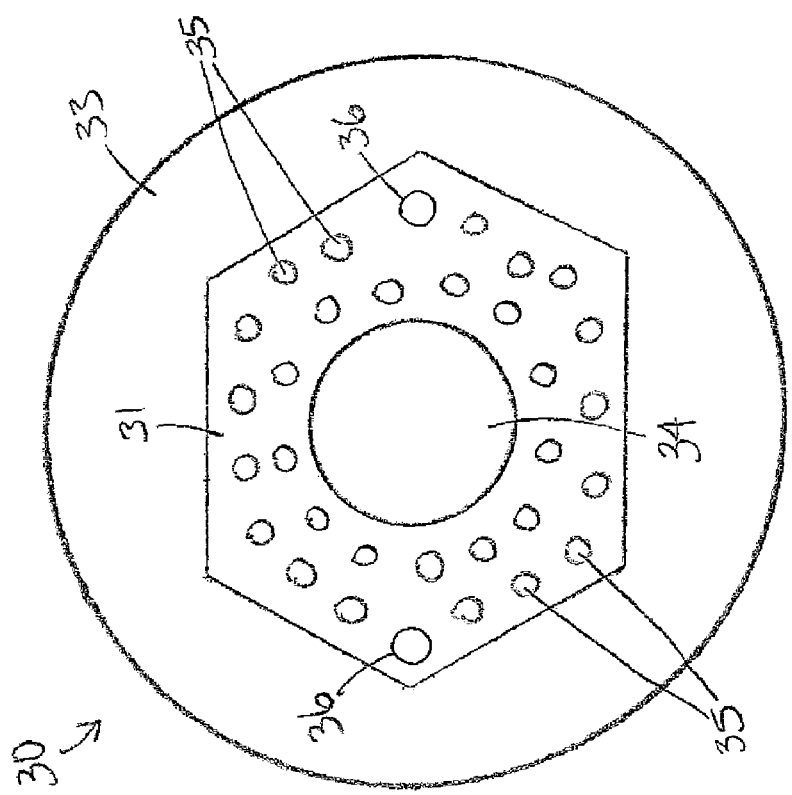
FIG. 3 shows an expanded view of an illustrative embodiment of a flexible bone fitting portion of an apparatus for delivering a bone reinforcing material.

FIG. 3 shows an alternate embodiment of the flexible bone fitting portion 30. In this embodiment, flexible bone fitting portion 30 further comprises a plurality of holes 35 that run through the bone fitting portion 30 for insertion of reinforcing materials including, but not limited to, flexible orthopedic wires, stainless steel rods, and metal pins 46. The introduction of reinforcing materials 46 to the bone void 42 may help the bone reinforcing mixture to form a tight union, producing a structure that is extra strong and resilient. Placement of the holes 35 on the flexible bone fitting portion 30 may be determined such that the strongest support structure is formed.

Not all embodiments require a bone fitting portion and in an embodiment, instruments and/or materials may be inserted directly into the bone via an opening in the bone itself, as not all embodiments are intended to be limited in this manner. In addition, the reinforcing materials may be introduced into the bone in any way, such as by forcing the reinforcing materials in, using a piston, using a hammer, using a gun or other methods known to those skilled in the art, as not all embodiments are intended to be limited in this manner.

Figure 4:
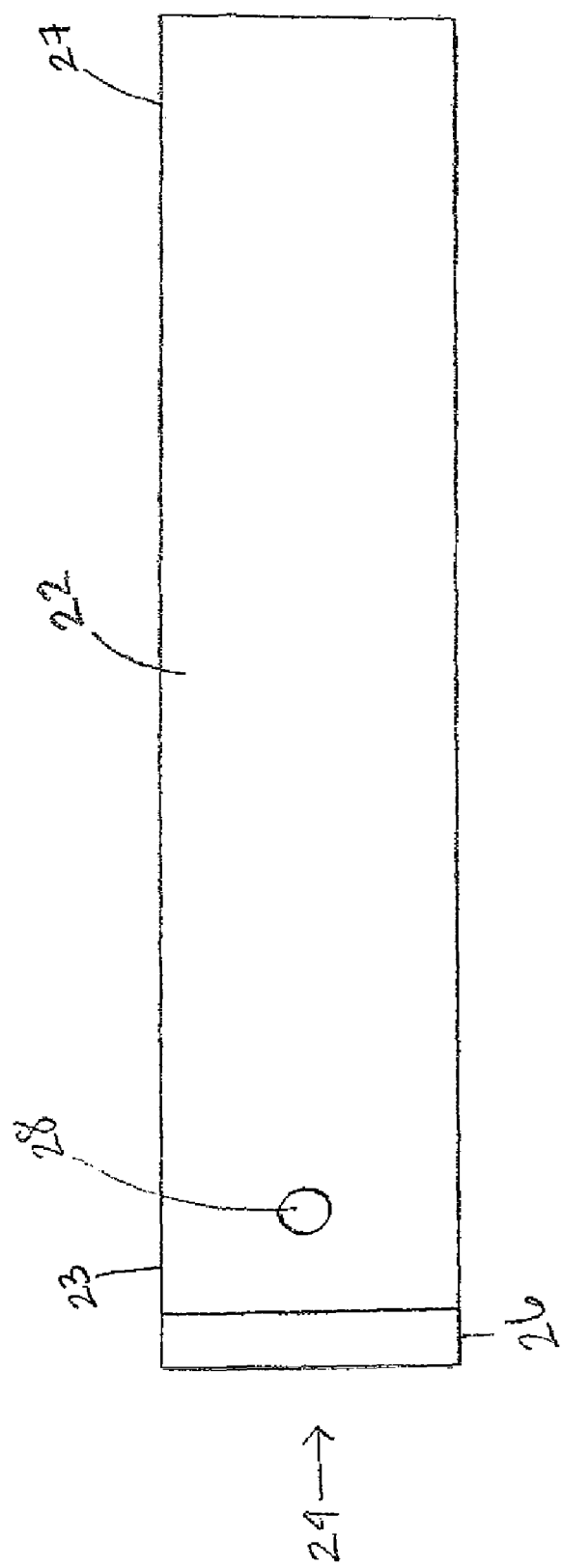
FIG. 4 shows an expanded view of an illustrative embodiment of an elongated flexible catheter of an apparatus for delivering a bone reinforcing material.

As shown in FIG. 4, the flexible tube 22 is a catheter having an elongated shaft with a proximal end 27, a distal end 23, and a longitudinal axis therebetween. The catheter includes as least one inner delivery lumen 24 which extends from the distal end 23 to the proximal end 27. In an embodiment there is one lumen. In an embodiment there are two lumens. In an embodiment there are three lumens. The distal end 23 of the catheter may include a radiopaque marker, band, or tip 26 which ensure easy visualization during catheter manipulation. At least one fenestration hole 28 may be included on the distal end 23 of the catheter 22, resulting in a larger area for the bone reinforcing mixture to exit the catheter 22 as well as precluding the potential for the lumen 24 of the catheter 22 to be occluded during insertion, with any residual debris, or to be clogged with the bone reinforcing mixture.

Figure 5:
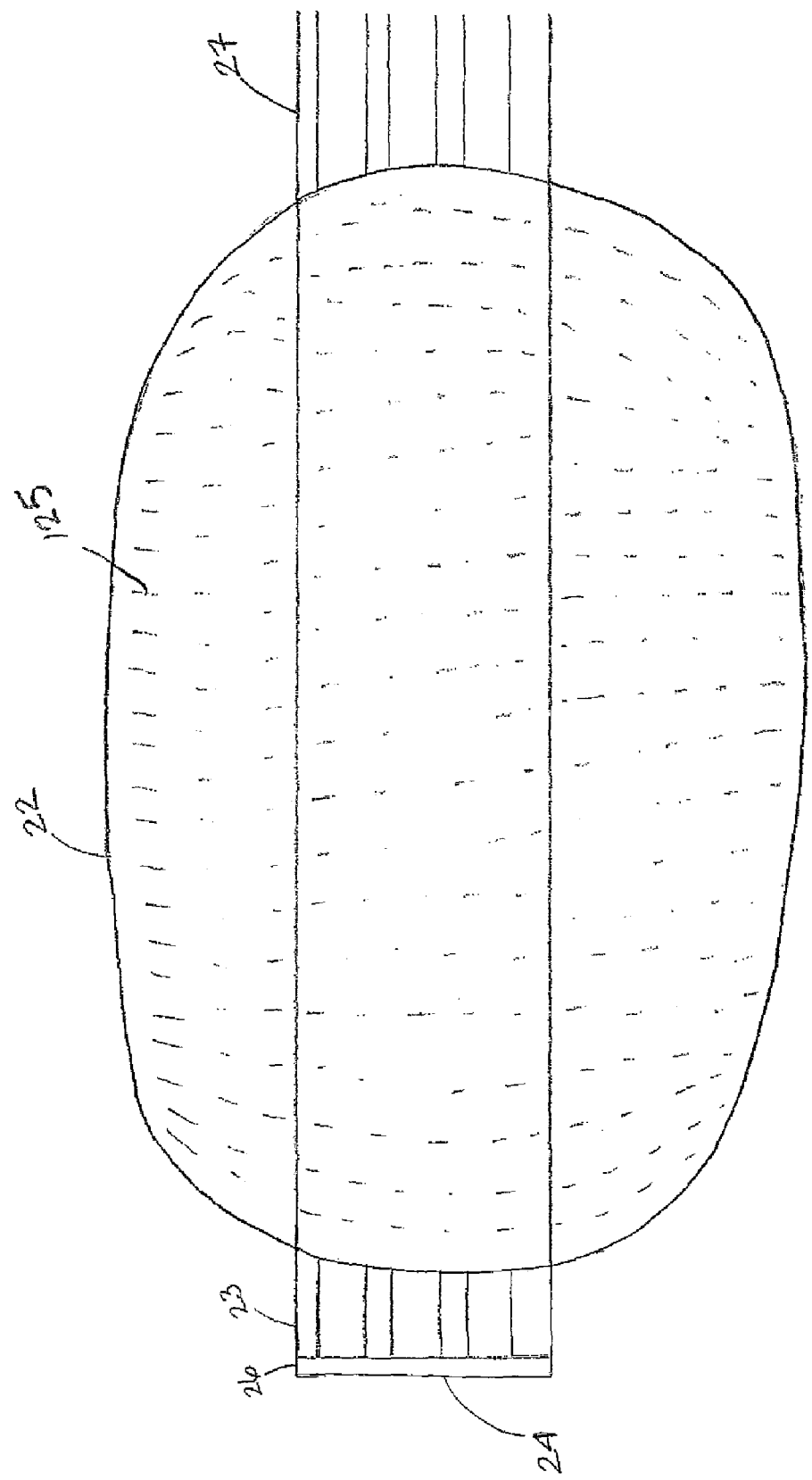
FIG. 5 shows an expanded view of an illustrative embodiment of an elongated flexible balloon catheter of an apparatus for delivering a bone reinforcing material.

As shown in FIG. 5, the flexible tube 22 is a balloon catheter having an elongated shaft with a proximal end 27, a distal end 23, and a longitudinal axis therebetween. The end of the catheter has a balloon portion that inflates and deflates and is used to hydraulically force the bone reinforcing mixture up against the wall of the bone void 42. The balloon catheter includes a plurality of inner delivery lumens 24 extending outward through a sidewall of the balloon portion and ending in a plurality of passageways 125 which act as delivery surfaces for the delivery of the bone reinforcing mixture. The plurality of passageways 125 may reside anywhere along the length of the balloon portion of the balloon catheter, for example, along the entire length of the balloon portion, as shown in FIG. 5. The distal end 23 of the balloon catheter may include the radiopaque marker, band, or tip 26 which may allow visualization, for example, by fluoroscopy, during catheter manipulation. The balloon catheter further includes a UV light source path, such as a fiber, that runs down the length of the balloon catheter, either inside the lumen 24, or on the outside of the catheter, and is able to cure the bone reinforcing mixture once it has been released from the plurality of passageways 125 to the bone void 42.

The deflated balloon catheter 22 is positioned in place in the bone void 42, then inflated to perform the necessary procedure, and deflated again in order to be moved to a different location in the bone void 42 or to be removed entirely from the bone void 42.

Figure 6:
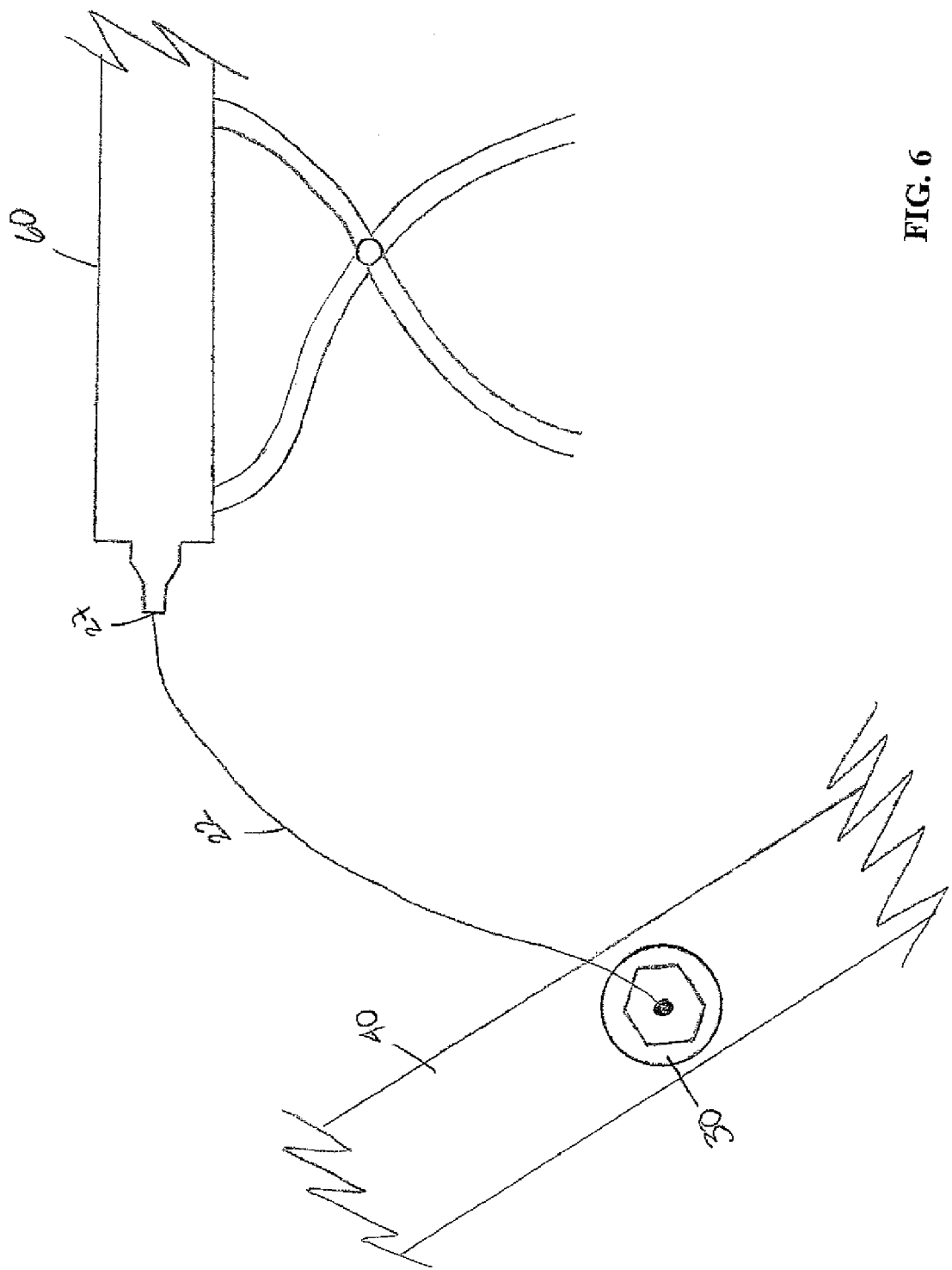
FIG. 6 shows a view of an illustrative embodiment of an apparatus for delivering a bone reinforcing material.

The proximal end of the flexible tube 22 may be attached to any adhesive system 60 known in the art to which the desired bone reinforcing mixture has been placed, as shown in FIG. 6. Examples of adhesive systems include, but are not limited to, caulking gun type systems, syringe systems, bag systems that contain the bone reinforcing material where the delivery of the bone reinforcing material is controlled using a tube clamp or any other restrictor valve.

Figure 7C:
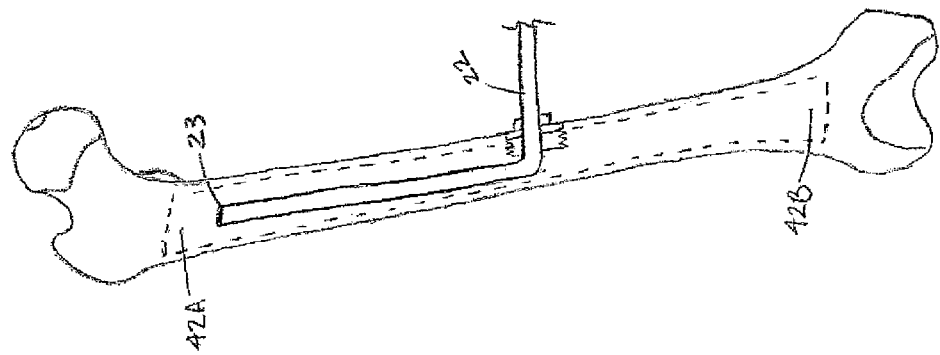
FIGS. 7A-7C show illustrative method steps for the placement of an apparatus for delivering a bone reinforcing material.

In using apparatus 20 of the presently disclosed embodiments, access to the bone 40 may be accomplished by a medical professional. As shown in FIG. 7A, the medical professional makes an incision through the skin to expose the bone 40. Once the bone 40 is exposed, it may be necessary to retract some muscles and tissues that may be in view of the bone 40. Penetration through the compact layer, the spongy layer and a portion of the medullary cavity of the bone 40 may be accomplished by any method known in the art and within the spirit and scope of the presently disclosed embodiments. In an embodiment, a bone drill bit is used to gain access through the compact layer, the spongy layer and a portion of the medullary cavity. The location of a bone penetration site 43 is typically distal to the location of a weakened area 45 by about 3 cm. In using a drill bit, it is desirable for the drill bit to be applied at an angle other than 90° to the bone, for example, at an angle of about 20° to about 45°. The drill bit may be aimed toward the crack line of the weakened area 45 in the bone 40.

Figure 7B:
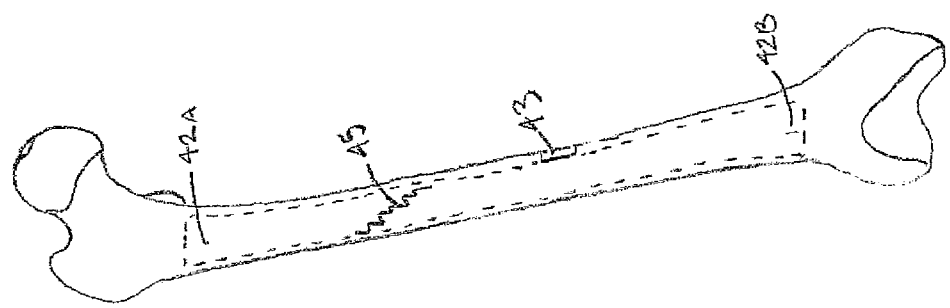
Figure 7A:
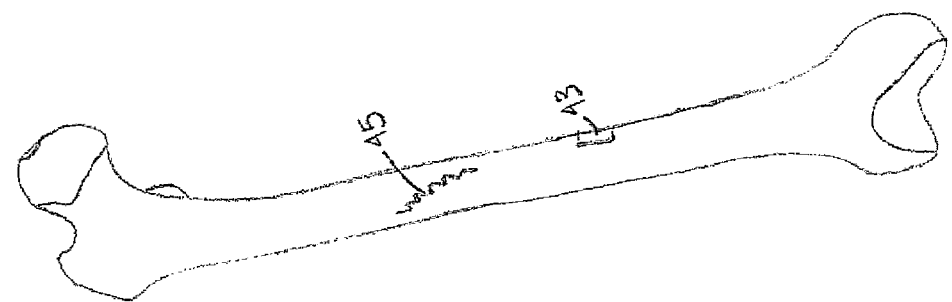

Once the medullary cavity is reached, the medullary material including air, blood, fluids, fat, marrow, tissue and bone debris needs to be completely removed to form a bone void 42 shown in FIG. 7B as a dashed line. The bone void 42 is defined as a hollowed out space, wherein position 42A defines the most distal edge of the bone void 42 with relation to the penetration point 43 on the bone 40, and position 42B defines the most proximal edge of the bone void 42 with relation to the penetration site 43 on the bone 40. The bone 40 may be hollowed out sufficiently to have all the medullary material of the medullary cavity up to the cortical bone removed. The length of medullary material removed will vary according to the area of weakened portion 45, but will typically include 3 cm above and 3 cm below the weakened portion 45 of the bone 40. There are many methods for removing the medullary material that are known in the art and within the spirit and scope on the presently disclosed embodiments. Methods include those described in U.S. Pat. No. 4,294,251 entitled "Method of Suction Lavage;" U.S. Pat. No. 5,554,111 entitled "Bone Cleaning and Drying System;" U.S. Pat. No. 5,707,374 entitled "Apparatus for Preparing the Medullary Cavity;" U.S. Pat. No. 6,478,751 entitled "Bone Marrow Aspiration Needle;" and U.S. Pat. No. 6,358,252 entitled "Apparatus for Extracting Bone Marrow."

The apparatus and method described herein is not limited to bones having a medullary cavity and may be used on an interior of any bone. For example, the bone void 42 may be a naturally occurring space, a previously created space or created by a user by, for example, removing bone marrow from the medullary cavity and/or creating a hole in the spongy or cancellous bone, as not all of the present embodiments are intended to be limited in this manner.

After the medullary material has been completely removed, the apparatus 20 may be positioned at the penetration site 43. The bone fitting portion 30 is threaded into the penetration site 43 and the flexible tube 22 is inserted through the insertion hole 34 of the bone fitting portion 30. If desired, reinforcing materials including, but not limited to, flexible orthopedic wires, stainless steel rods, and metal pins 46 may be added to the bone void 42 before the flexible tube 22 is placed in the bone fitting portion 30. The introduction of reinforcing materials 46 to the bone void 42 may help the bone reinforcing mixture to form a tight union, producing a structure that is extra strong and resilient.

As shown in FIG. 7C, the flexible tube 22 is a catheter. The catheter is positioned so that the distal end 23 is at the most distal edge 42A of the bone void 42. The radiopaque marker 26 allows the medical professional to view the distal end 23 of the catheter using fluoroscopy techniques. Once the correct positioning of the catheter has been determined, the proximal end 27 of the catheter may be attached to a caulking gun type adhesive system which contains a desired bone reinforcing mixture. The bone reinforcing mixture may be a natural or synthetic material for strengthening, replacing or reinforcing of bones or bone tissue. Bone reinforcing mixtures include glues, adhesives, cements, hard tissue replacement polymers, natural coral, hydroxyapatite, beta-tricalcium phosphate, and various other biomaterials known in the art for strengthening, replacing or reinforcing bones. As inert materials, bone reinforcing mixtures can be incorporated into surrounding tissue or gradually replaced by original tissue. Those skilled in the art will recognize that numerous bone reinforcing mixtures known in the art are within the spirit and scope of the presently disclosed embodiments.

The electromagnetic spectrum is the range of all possible electromagnetic radiation. The electromagnetic spectrum of an object is the frequency range of electromagnetic radiation that it emits, reflects, or transmits. The electromagnetic spectrum extends from just below the frequencies used for modern radio (at the long-wavelength end) to gamma radiation (at the short-wavelength end), covering wavelengths from thousands of kilometers down to fractions of the size of an atom. Ultraviolet (UV) light wavelength ranges from about 1 nm to about 380 nm, and can be subdivided into the following categories: near UV (380-200 nm wavelength; abbreviated NUV), far or vacuum UV (200-10 nm; abbreviated FUV or VUV), and extreme UV (1-31 nm; abbreviated EUV or XUV). Similarly, visible light has a wavelength spectrum of between about 380 to about 780 nm.

Light Cured Materials (LCMs) utilize energy provided by ultraviolet (UV) or visible light. Being very energetic, UV light can break chemical bonds, making molecules unusually reactive or ionizing them, in general changing their mutual behavior. In an embodiment, a light emitted by a light source reacts with a photoinitiator sensitive to UV light or visible light. Photoinitiators provide important curing mechanisms for addition polymerization.

Using a UV light, the reinforcing material ensures there is no or minimal thermal egress and that the thermal egress may not be long in duration. More specifically, there is no chemical composition or mixing of materials. The introduction of light starts the photoinitiator and the glue hardens. Once the light is introduced, the material inside the bone hardens and the materials inside are affixed in place. Until the light is introduced, the bone placement is not disturbed or rushed as there is no hardening of a glue until the light is introduced. The glue may be infused or removed from the bone void due to the low viscosity of the material. In an embodiment the viscosity of the reinforcing material is less than approximately 1000 cP. Not all embodiments are intended to be limited in this respect and some embodiments may include reinforcing materials having a viscosity exactly equal to or greater than 1000 cP.

Different light cured materials use photoinitiators sensitive to different ranges of UV and visible light. For example, visible blue light may be useful to the curing process as it allows materials to be cured between substrates that block UV light but transmit visible light (e.g., plastics). Visible light increases the cure speed of light cured materials since a greater portion of the electromagnetic spectrum is available as useful energy. Further, visible light penetrates through light cured materials to a greater depth-enhancing cure depth. The light cured materials cure in such a way that is sufficient to hold a bone in the correct orientation. More specifically, the ability to inflate, set, adjust, orient bones, and the resulting union of the bone are available prior to hardening the glue. Examples of light cured materials include those commercially available from Loctite of Henkel Corporation, located in Rocky Hill, Conn.

In an embodiment, a liquid adhesive such as a cationic epoxy having a cationic photo-initiator is used. A pre-activated epoxy exhibits a very low shrink rate. To activate, a UV light in about 245 nm to about 365 nm range is applied to an epoxy and starts a cure reaction. Once the cure reaction is started, that reaction continues to completion (e.g., even in the dark).

In an embodiment, the reinforcing material is a bioabsorbable epoxy so the hardened epoxy is absorbed into the body over time. In an embodiment, the reinforcing material is cured by chemical activation or thermal activation. Chemical activation includes but is limited to water or other liquids. In an embodiment, the reinforcing material is a drying adhesive which has a polymer dissolved in a solvent such that as the solvent evaporates, the adhesive hardens. In an embodiment, the reinforcing material is a hot or thermoplastic adhesive such that as the adhesive cools, the adhesive hardens. The reinforcing material is not limited to the embodiments described herein and may be any material that reinforces the bone. Some materials may require or be enhanced by curing via any means, such as UV or visible light, heat, and/or addition or removal of a chemical or substance, may utilize any outside or internal processes to cure the material, or may not require curing.

In an embodiment, the bone reinforcing mixture is a light cure adhesive (or UV adhesive). A benefit of ultraviolet (UV) curing is that it is a cure-on-demand process and that adhesives may be free of solvents and include environmentally friendly resins that cure in seconds upon exposure to long wave UV light or visible light. In an embodiment, the UV adhesive is a single-component, solvent-free adhesive that will not cure until a UV light engages the adhesive, and when that occurs, the adhesive will cure in seconds to form a complete bond with a shear strength. Visible light penetrates through the epoxy to a greater depth. Since the visible light penetrates through the epoxy, curing of the material increases as a greater portion of the electromagnetic spectrum is available as useful energy. In this way, light cured materials utilize energy provided by ultraviolet light or visible light to start a curing process. Light emitted by a source reacts with a photoinitiator sensitive to UV light or to visible light. Visible light allows materials to be cured between substrates that block UV light but transmits visible light. Using the UV light to cure the reinforcing material assists in holding broken bones in place, assists in filling the bone void, and enables viewing under a C arm imaging system.

Those skilled in the art will recognize that some light cured materials may be activated by UV light, visible light, x-rays, gamma rays, microwaves, radio waves, long waves or any light having a wavelength less than about 1 nm, between about 1 nm and about 380 nm, between about 380 nm and about 780 nm, or greater than about 780 nm, as not all embodiments are intended to be limited in that respect.

Several epoxies known in the art are suitable for use as bone reinforcing materials and vary in viscosity, cure times, and hardness (durometer or shore) when fully cured. A durometer of a material indicates the hardness of the material, defined as the material's resistance to permanent indentation. Depending on the amount of resultant support that is necessary for a given bone fracture, a specific durometer UV adhesive may be chosen. Alternately, multiple UV adhesives having varying durometers may be chosen for the repair of a bone fracture and be within the scope and spirit of the presently disclosed embodiments. The durometer of a material may be altered to achieve either greater rigidity or a more malleable result. The shore or durometer of the epoxies may also be varied in a layer-by-layer approach to achieve a softer more malleable outer layer or a rigid internal structure. The shore or durometer may also be altered to ensure the interface between the glue and the bone is flexible similar to natural shock absorption.

The mechanical properties of the epoxies dictate using methods/measures that are typical for high-strength and high-impact materials including but not limited to, tensile strength and tensile modulus, tensile strength tests, ultimate modulus, Poisson's ratio, hardness measurements like Vickers and Charpy Impact which measures yield strength and toughness.

In an embodiment, the epoxy has an elastic modulus of about 0.1 to about 50 GPa, preferably about 1 to about 10 GPa. Cranial-facial bones have an elastic modulus of about 20 GPa, while plexiglass (PMMA, i.e. bone cement) has an elastic modulus of about 1 to about 2 GPa. Typical epoxies have an elastic modulus in the range of about 1 to about 3 GPa, but nano-modified epoxies can have about a 3-5 fold or more increase over the original epoxy with only a few percent loading of carbon nanotubes, clay, mica, and other structures.

In an embodiment, carbon nanotubes (CNTs) are added to the reinforcing material to increase the strength of the glue. Carbon nanotubes are an allotrope of carbon that take the form of cylindrical carbon molecules and have novel strength properties. Carbon nanotubes exhibit extraordinary strength. Nanotubes are members of the fullerene structural family, which also includes buckyballs. Whereas buckyballs are spherical in shape, a nanotube is cylindrical with at least one end typically capped with a hemisphere of the buckyball structure. Nanotubes are composed entirely of sp2 bonds, similar to those of graphite. This bonding structure, which is stronger than the sp3 bonds found in diamond, provides the molecules with their unique strength. Nanotubes naturally align themselves into "ropes" held together by Van der Waals forces. Single walled nanotubes or multi-walled nanotubes may be used to strengthen the reinforcing materials.

The catheter is attached to the delivery system which contains the bone reinforcing mixture and the bone reinforcing mixture is infused through the catheter. The infusion of the bone reinforcing mixture may cause pressure buildup in the bone void 42, which may be controlled so that damage to the existing bone 40 is prevented. The bone fitting portion 30 comprises at least one pressure relief valve 36 for relieving any pressure buildup in the bone void 42 during the delivery of the bone reinforcing mixture. The introduction of the bone reinforcing mixture occurs at the most distal edge of the bone void 42A and works backward towards the penetration site 43. The catheter is slowly moved backward toward the penetration site 43 and the medical professional is slowly withdrawing bone reinforcing mixture from the catheter. By rotating the bone fitting portion 30, the directionality of the delivery of the bone reinforcing mixture can be made and complete filling of the bone void 42 is ensured. The use of the pressure relief valve 36 on the bone fitting portion 30 allows for the complete filling of the bone void 42 and the egress of excess bone reinforcing mixture out of the pressure relief valve 36 indicates complete bone reinforcing mixture delivery.

The reinforcing materials used, supports and strengthens the remaining bone 40 to prevent further weakening of the bone 40. In addition, the reinforcing materials anchor the bone 40 that is fractured, helping to stabilize the bone 40 for repair. The viscosity of the bone reinforcing mixture is designed to settle and allow any air bubbles to rise to the top/rear portion where the penetration site 43 is, letting air escape and more bone reinforcing mixture to be added as necessary. Once the entire bone void 42 has been filled with bone reinforcing mixture, which is indicated by excess bone reinforcing mixture regressing out of the pressure relief valve 36, the catheter 22 is removed from the bone fitting portion 30. Minor pressure may be applied to ensure that the displaced bone reinforcing mixture from the catheter 22 is filled with new bone reinforcing mixture. At the completion of the infusion process, the bone fitting portion 30 is unscrewed and removed from the bone 40 and a small plug of bone reinforcing mixture is used to seal the rest of the bone void 42. The repair of the fracture is far less invasive then prior techniques and the delivery of bone reinforcing mixture is easily controlled.

Figure 8A:
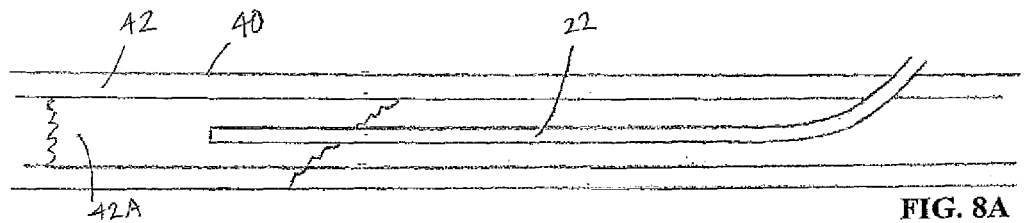
FIGS. 8A-8F show illustrative method steps for the placement of an apparatus for delivering a bone reinforcing material.

As shown in FIG. 8A, the flexible tube 22 is a balloon catheter which is inserted through the insertion hole of the bone fitting portion in a deflated state. The balloon catheter is positioned so that the distal end 23 of the balloon catheter is at the most distal edge 42A of the bone void 42. The proximal end of the balloon catheter may be attached to a caulking gun type adhesive system which contains a desired bone reinforcing mixture. As described above with respect to the methods depicted in FIGS. 7A-7C and as will be described further below, the bone reinforcing mixture may be any material that assists in strengthening, replacing or reinforcing bones or bone tissue.

Figure 8B:
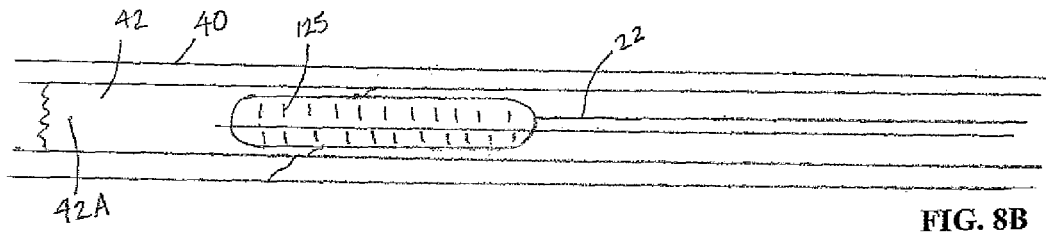
Figure 8C:
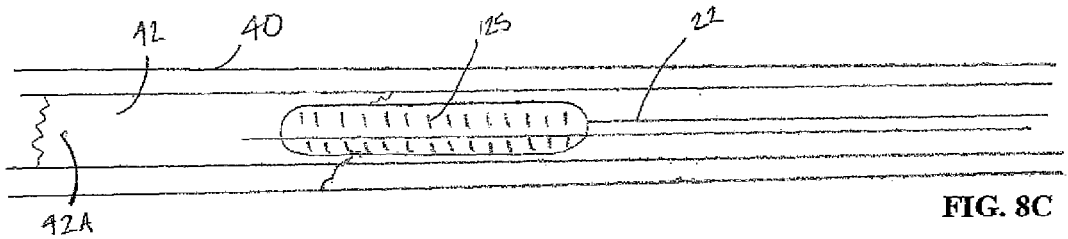
Figure 8D:
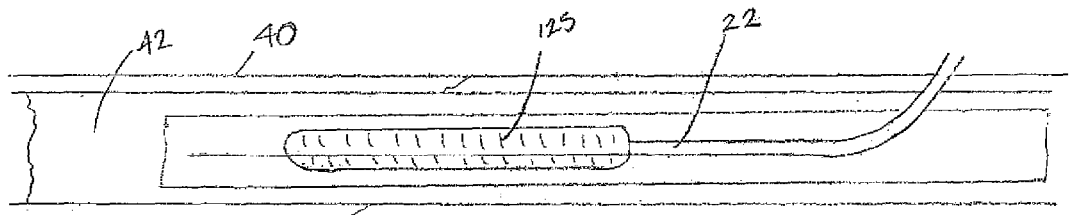
Figure 8E:
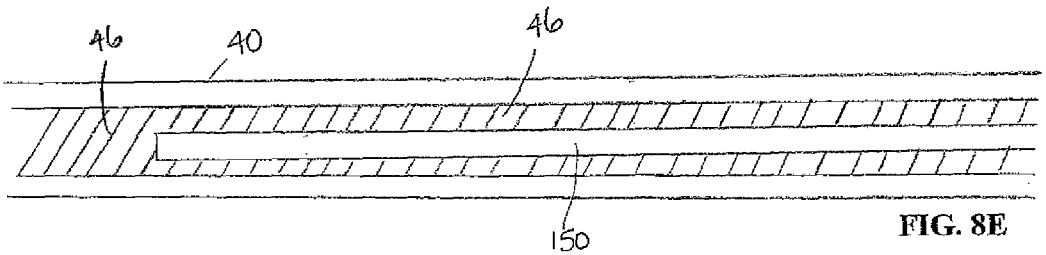
Figure 8F:
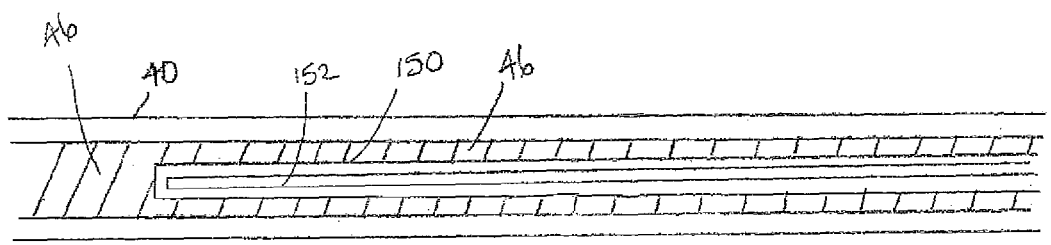

After the balloon catheter is attached to the delivery system which contains the bone reinforcing mixture, the bone reinforcing mixture is infused through one of the lumens of the balloon catheter. In an embodiment the bone reinforcing mixture is a UV adhesive which requires a UV light source to cure the adhesive. The balloon portion is then inflated, as shown in FIG. 8B, and the UV adhesive is released through the plurality of passageways 125 running along the sidewall of the balloon portion. The UV adhesive may also be released through the inner lumen. The UV adhesive is pushed or compressed, in a hydraulic-like fashion, up against the wall of the bone void 42. The UV light source path is illuminated which cures the UV adhesive. The balloon portion of the catheter is then slightly deflated followed by infusion of the same or a different UV adhesive delivery system through a different lumen of the balloon catheter. The balloon portion is then re-inflated and the UV adhesive is released through the plurality of passageways 125, as shown in FIG. 8C. The UV adhesive is pushed or compressed, in a hydraulic-like fashion, up against the UV adhesive that has been cured prior. The UV light source path is illuminated which cures the UV adhesive. The balloon portion of the catheter is then slightly deflated followed by infusion of the same or a different UV adhesive delivery system through a different lumen of the balloon catheter, as shown in FIG. 8D. The bone void 42 is being reinforced from the walls inward creating a shell or layer by layer repair producing a strong, resilient union, as shown in FIGS. 8B-8D. The process is repeated until most of the space in the bone void 42 has been filled with UV adhesive, followed by the removal of the balloon catheter, as shown in FIG. 8E. A central space 150 remains in the bone void 42 which may be filled in order to provide the strength and support to the bone 40. An optical rod, such as a fiber rod, or similar device 152 may be positioned in the central space 150 and turned on, or illuminated, as shown in FIG. 8F. The UV light will then harden the remaining UV adhesive in the bone void 42. The end of the optical rod 152 may be cut and remain in the bone void 42.

The light curing adhesives, such as UV curing adhesives, use light, such as ultraviolet light, to initiate curing that allows a bond without heating. Drugs (for example, antibiotics), proteins (for example, growth factors) and or other natural or synthetic additives may be used with the adhesive delivery system. For example, after a minimally invasive surgical procedure an infection may develop in the patient, requiring the patient to undergo antibiotic treatment. An antibiotic drug may be added to the adhesives of the presently disclosed embodiments to help combat a possible infection. Proteins, such as, for example, the bone morphogenic protein or other growth factors have been shown to induce the formation of cartilage and bone. A growth factor may be added to the adhesives to help induce the formation of new bone.

In an embodiment, glue is infused through a lumen in the catheter to assist in positioning the bone in a healing orientation. In an embodiment, glue is infused through a lumen in the catheter to expand a balloon to position the bone in a healing orientation. To establish the healing orientation, the balloon inflates until the bones move into an aligned orientation. Orientation of the bones may be done without any visualization of the process or using x-ray or a fluoroscope. A C arm imaging system is a fluoroscope that may allow movement or manipulation of the fluoroscope to rotate around tissue while viewing. Other techniques can be used for monitoring or inspecting the delivery or use of the balloon such as magnetic resonance imaging (MRI), ultrasound imaging, x-ray fluoroscopy, Fourier transform infrared spectroscopy, ultraviolet or visible spectroscopy. In an embodiment, the balloon is composed of non ferromagnetic materials and, thus, is compatible with MRI.

Once the glue is hardened, the glue has the appropriate tensile strength, yield, elongation, and other properties to ensure a good bonding of the bone-to-bone repair and maintain strength for healing bone for at least about six weeks. An intramedullary pin or rod is created to hold the bone in a proper healing orientation. The implantable intramedullary rod or pin is capable of being inserted into the bone without driving or insertion force. In an embodiment, the glue mixture has a viscosity of about cP 1000 or less. A contrast material could be added to the glue mixture without significantly increasing the viscosity. Contrast material including, but not limited to, barium sulfate, tantalum, or other contrast materials known in the art. In this way, the glue mixture may be used with a smaller lumen during delivery.

Many glues have a specific cure time dependant upon time and temperature after which the glue enters the plastic region. The disclosed glues cure substantially instantaneously upon activation of a light source allowing a desired amount of glue in a precise location that can cure once struck by incident light. Although light-cured glues are disclosed, any type of glue may be used such as those that cure in response to light, heat, a chemical interaction, air, oxygen, any other activator or cure with time, as not all embodiments described herein are intended to be limited in this manner.

In an embodiment, a plurality of light guides engage the light source. In an embodiment, the light guide is a flexible light pipe. The light guide directs light from a light source to the bone void. Because the light source is larger than the diameter of the catheter, a light taper is used to direct the light. An optical taper may be used for focusing the light from a light source into a smaller catheter. In an embodiment, an optical taper is a shaped bundle of optical fibers having a light source that is concentrated at a proximal end. In an embodiment, the catheter also includes a taper holder, a light shield, a fiber boss, a handle, illumination bundles having diameters, for example, of 0.5 mm, 0.75 mm, 1.0 mm, 1.25 mm and/or 1.5 mm, and a polyimide sheathing.

In an embodiment, an optical taper is a single or "multi-element" rod of optical fibers. When a single or multi-element rod is tapered, the resulting optical characteristic of the rod changes to reduce the Numerical Aperture (NA) of the normal end, while maintaining the original Numerical Aperture at the tapered end. The Numerical Aperture of an optical system is a dimensionless number that characterizes the range of angles over which the system can accept or emit light. The amount of change is a ratio of the diameters. When light enters the small end of a taper at a full acceptance angle, the emerging beam at the other end may be collimated as compared to the original range of entry angles. In an embodiment, a catheter has an interface with an optical taper. In an embodiment, the optical taper engages the catheter and is for a single use and disposable. In an embodiment, the optical taper engages the light source and may be used for multiple procedures.

In an embodiment, using an optical taper shapes a concentration of a light beam at the proximal end of the catheter. A disposable section of catheter fibers may be aligned to the taper to improve quality. An optical taper also may provide an appropriate mating point for a disposable piece. One advantage of using an optical taper is that the design of a catheter is simpler because small optical fibers are aligned under a larger optical taper. Since the small optical fibers are aligned under a larger optical taper, alignment is not as important.

A plurality of illumination fibers may be collected by mechanical connectors including, but not limited to, a metallic ring, a polymer ring using glue or similar structures. After the fibers are bound together, the fibers may be cut in an even manner. The light fibers may be polished smooth to assist in pointing light illumination. In an embodiment, the optical taper is mounted adjacent to a light fiber bundle with a tapered end that may be in contact with polished ends of the fibers.

One or more radiopaque markers may be placed on the catheter and/or the balloon. In an embodiment, the radiopaque marker is located at the distal end of the catheter. The radiopaque marker, using radiopaque material such as barium sulfate, tantalum, or other materials known to increase radiopacity, allows the medical professional to view the distal end of the catheter using fluoroscopy techniques. The radiopaque material provides visibility during insertion to determine the precise positioning of the catheter and/or balloon during placement and inflation. The radiopaque material permits visualization of voids created by air entrapped in the bone void. In an embodiment, the radiopaque material permits visualization to preclude the balloon from misengaging or not meeting the bone due to improper inflation to maintain a uniform balloon/bone interface. Once the correct positioning of the catheter and/or balloon is determined, the proximal end of the catheter may be attached to a caulking gun type adhesive system which contains a bone reinforcing mixture.

One or more radiopaque markers on the proximal end and distal end of the catheter and/or balloon may be used to determine the position of the catheter and/or balloon within the bone to ensure correct location of the catheter and/or balloon through the use of an x-ray or fluoroscope. As the reinforcing material is introduced, the multiple sections of bones are brought into a healing orientation and in a stable configuration. If the bone is in the healing orientation, illumination is provided via illumination fibers within the catheter and/or balloon. In an embodiment, a plurality of illumination fibers are used to provide sufficient light to cure the reinforcing material in the bone.

After the reinforcing material in the bone void is cured, such as by using the illumination fibers, an illumination band located, for example, at the balloon/catheter junction may be activated causing light to cure the epoxy located in the catheter within the illumination band. The illumination band is located adjacent to the distal end of the catheter, for example, at the junction between the catheter and the balloon. The illumination band extends around the catheter and has a stress concentrator. The stress concentrator may be a notch, groove, channel or similar structure that concentrates stress in the illumination band. The stress concentrator of the illumination band may be notched, scored, indented, pre-weakened or pre-stressed to direct separation of the balloon from the catheter under specific torsional load. A delivery catheter may use light guides composed of silica, silicon, or polymer materials that transmit light of the proper frequency to the illumination band.

In an embodiment, the distal end of the catheter may contain glue that is hardened to form a separation area. The separation area ensures that there are no glue leaks from the catheter and/or the balloon. The separation area seals the catheter and/or balloon and removes the delivery catheter by making a break at a known or predetermined site (e.g., a separation area). The separation area is located where the distal end of the catheter meets the proximal end of the balloon because the glue in the balloon is hardened after activation of the illumination band. The separation area may be various lengths and up to about an inch long. When torque is applied to the catheter, the catheter separates from the balloon. Twisting the catheter creates a torque sufficient in the separation area to break the catheter from the balloon. The twisting creates a sufficient shear to break the residual glue and create a clean separation of the catheter/balloon interface. Because the reinforcing mixture in the separation area has been cured and hardened by the illumination band, no reinforcing mixture can leak into the body from the catheter and/or the balloon.

In an embodiment, the illumination band is connected to a light guide. In an embodiment, safety measures prevent accidental or inadvertent illumination. The illumination band is activated by a separate switch which is the active process that the user takes to connect the light to be delivered. Having a distinct switch to activate the illumination band may help to prevent inadvertent delivery of light from the light source to cure the reinforcing material. In an embodiment, the switch is a mating device such as a rotating band or rotating fuse that is rotated to activate the illumination band causing illumination on the reinforcing material within the catheter to cure the area adjacent to the illumination band. Once the illumination band is activated, a section of the infusion catheter is sealed with the UV curable epoxy proximal and distal to the illumination band. The activation of the illumination band seals the most proximal end of the balloon, seals the distal end of the catheter, and ensures that there is a "hard seal" of the glue at the illumination band allowing no glue to leak from the balloon or the catheter.

In an embodiment, the catheter is cut to separate the balloon from the catheter. A device slides over the catheter and allows a right angle scissor to descend through the catheter and make a cut. The location of the cut may be determined by using a fluoroscope or an x-ray. In an embodiment, the cut location is at the terminal end of the introduction site where the catheter meets the balloon.

In an embodiment, a fracture repair process reinforces a weakened or fractured bone without exposing the bone through a traditional surgical incision (e.g., greater than about 10 mm). The presently disclosed embodiments use a minimally invasive approach by making a minor incision to gain access. Minimally invasive refers to surgical means, such as microsurgical, endoscopic or arthroscopic surgical means, that can be accomplished with minimal disruption of the pertinent musculature, for instance, without the need for open access to the tissue injury site or through minimal incisions. Minimally invasive procedures are often accomplished by the use of visualization such as fiber optic or microscopic visualization, and provide a post-operative recovery time that is substantially less than the recovery time that accompanies the corresponding open surgical approach.

Some of the presently disclosed embodiments are minimally invasive and minimize the cutting of surrounding tissue while implanting a bone fixator within the intramedullary cavity. By restoring and preserving bone structure, some of the presently disclosed embodiments permit additional future treatment options. Benefits of minimally invasive procedures include causing less trauma because there is minimal blood loss, a reduction in surgery and anesthetized time, shortened hospitalization, and an easier and more rapid recovery.

Figure 9B:
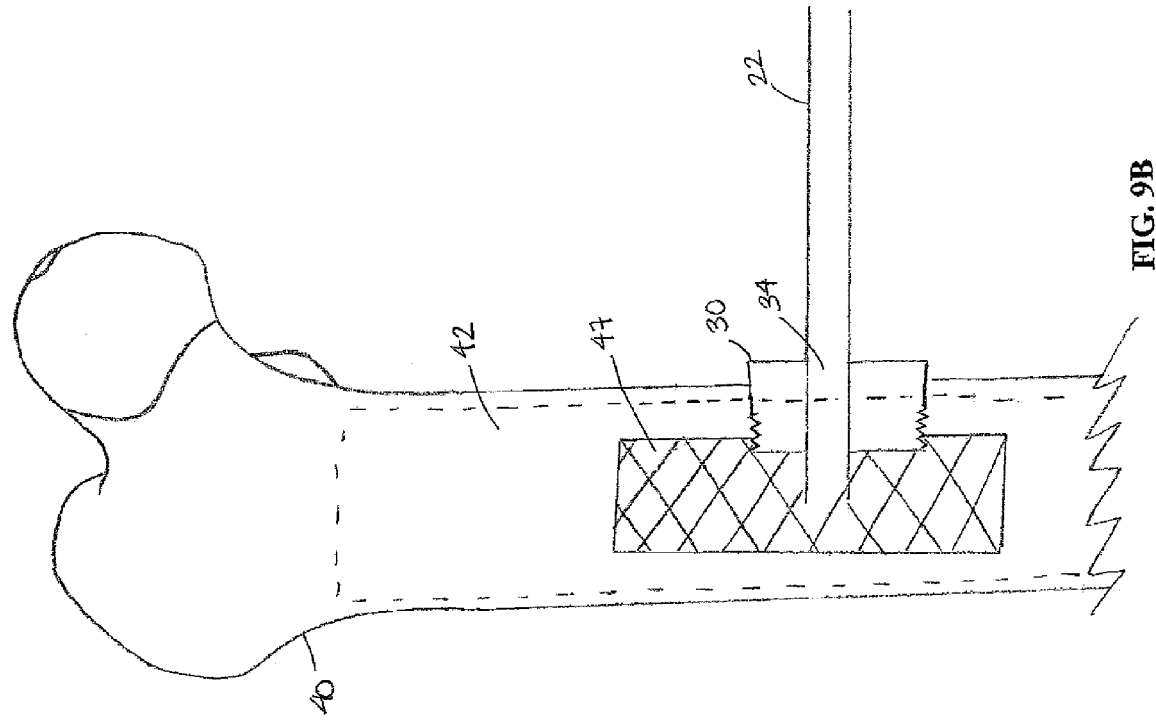
FIG. 9B shows a view of the self-expanding device of FIG. 9A in use.
Figure 9A:
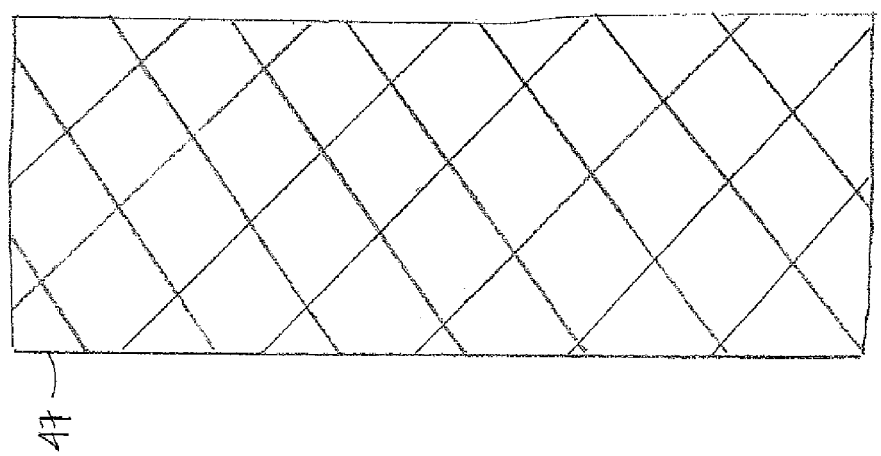
FIG. 9A shows an expanded view of an illustrative embodiment of a self-expanding device that may be used with an apparatus for delivering a bone reinforcing material.

The opening or central hole 34 of the bone fitting portion 30 is capable of accepting a variety of surgical instruments including, but not limited to, catheters, radial structural members, stents, stent-like devices, cannulas, orthopedic wires, stainless steel rods, metal pins and other devices. FIG. 9A shows an example of a self-expandable device 47 made from a material such as Nitinol wire which can be used to provide structure and support for a bone reinforcing mixture that is delivered to the bone void 42 using the disclosed embodiments. As shown in FIG. 9B, the flexible tube 22 is placed through the central hole 34 and the self-expandable device 47 is collapsed and brought through the flexible tube 22 and positioned within the bone void 42 where the self-expandable device 47 will resume the expanded shape to provide structure. The bone reinforcing mixture may then be added to the bone void 42 using the disclosed embodiments.

A method for reinforcing a bone in the body includes penetrating the bone at a site adjacent to a weakened or fractured area of the bone to gain access to a medullary cavity containing a medullary material; removing the medullary material located in the medullary cavity to form a bone void having a distal edge and a proximal edge; inserting a flexible bone fitting portion at the penetration site, the flexible bone fitting portion having a central hole, a threaded portion for insertion into the bone, and at least one pressure relief valve; positioning a catheter having a proximal end, a distal end, and a longitudinal axis therebetween through the central hole of the flexible bone fitting portion so the distal end of the catheter is within the bone void; infusing a bone reinforcing mixture through at least one inner lumen of the catheter into the bone void; and removing the catheter from the flexible bone fitting portion.

The method for reinforcing bone further comprises attaching an adhesive system containing the bone reinforcing mixture to the proximal end of the catheter. The method for reinforcing bone further comprises moving the catheter towards the proximal edge of the bone void and infusing the bone reinforcing mixture through the catheter. The method for reinforcing bone further comprises adding the bone reinforcing mixture until the bone reinforcing mixture has filled the bone void. The method for reinforcing bone further comprises inserting reinforcing materials into the bone void before positioning the catheter through the central hole, the reinforcing materials providing structure and support for the bone reinforcing mixture. The method for reinforcing bone further comprises allowing the bone reinforcing mixture to harden and removing the flexible bone fitting portion from the bone. The method for reinforcing bone further comprises sealing the penetration site.

A method for reinforcing a bone includes penetrating the bone at a site adjacent to a weakened or fractured area of the bone to access a medullary cavity of the bone; removing a medullary material located in the medullary cavity to form a bone void having a distal edge and a proximal edge; inserting a flexible bone fitting portion at the penetration site, the flexible bone fitting portion having a central hole, a threaded portion for insertion into the bone, and at least one pressure relief valve; positioning a catheter having a balloon portion through the central hole of the flexible bone fitting portion, wherein the catheter has a plurality of inner delivery lumens extending outward through a sidewall of the balloon portion and ending in a plurality of passageways; infusing the bone reinforcing mixture through the catheter to release the bone reinforcing mixture through the plurality of passageways; inflating the balloon portion to compress the bone reinforcing mixture against a wall of the bone void; activating a UV light source to harden the bone reinforcing mixture; removing the catheter from the bone fitting portion to yield a central space; and inserting an optical rod into the central space and illuminating the rod to harden any remaining bone reinforcing mixture.

The method for reinforcing bone further comprises attaching an adhesive system containing the bone reinforcing mixture to the proximal end of the catheter. The method for reinforcing bone further comprises deflating the balloon portion followed by infusing the bone reinforcing mixture to release the bone reinforcing mixture through the plurality of passageways. The method for reinforcing bone further comprises positioning a self-expandable device over the catheter while the balloon portion is deflated. The method for reinforcing bone further comprises cutting an end of the optical rod.

In an embodiment, a catheter may be constructed in a "Y" shape having two arms extending from a longer base. The longer base of the Y shaped catheter is inserted into the bone. A first upper arm of the Y shape engages a syringe. A second upper arm of the Y shape engages a light source. An optical taper may be used and is located between the light source and the catheter. In an embodiment, an outside circumference of the catheter ranges from about 3 French to about 8 French. In an embodiment, using a catheter of about 3 French to about 8 French, results in an inflated diameter of the balloon of about 2 mm to about 30 mm inflated diameter, as appropriate for the internal lumen of the bone.

In an embodiment, the catheter can be constructed of illumination materials resulting in a light transmittable fiber catheter which would not require illumination fibers or light guides. The catheter may have a wide variety of properties including, but not limited to, fiber type, fiber orientation, and resin matrix of the composite structure.

In an embodiment, the reinforcing material is pre-formed into a customized shape. A pre-determined shape or mold may be filled with the reinforcing material and the shaped material may be inserted into the body. In an embodiment the shaped material is further cured using one of the processes described above, such as UV light curing. In an embodiment, the material is partially or completely cured while in the mold and inserted into the body intact.

The apparatus may be used for delivering reinforcing materials into a weakened or fractured bone. For example, the presently disclosed embodiments may deliver reinforcing materials to a wrist fracture of a radius, an ulna or other wrist and hand bones, which may result in a wrist reduction.

The wrist is a collection of many joints and bones that allow use of the hands. The wrist has to be mobile while providing the strength for gripping. The wrist comprises at least eight separate small bones called the carpal bones, that connect the two bones of the forearm, called the radius and the ulna, to the bones of the hand and fingers. The metacarpal bones are the long bones that lie mostly underneath the palm, and they are in turn attached to the phalanges, the bones in the fingers and thumb. The wrist is complicated because every small bone forms a joint with its neighbor. Ligaments connect all the small bones to each other, and to the radius, ulna, and metacarpal bones. A wrist injury, such as falling on the outstretched hand, can damage these ligaments and change the way the bones of the wrist work together. The wrist can be injured in numerous ways. Some injuries seem to be no more than a simple sprain of the wrist when the injury occurs, but problems can develop years later. The joints are covered with articular cartilage that cushions the joints. A more serious injury, such as a fracture of one or more bones of the wrist, can injure the articular cartilage surfaces of the joints and lead to degenerative arthritis.

Distal radius fractures are common injuries that occur at the distal end of the wrist, where the wrist joint lies. The most common form of wrist fracture causes the radius to bend away from the palm. There may be a change in shape of the wrist, which is called the "dinner fork" deformity after its shape.

The most common cause of wrist fractures is when an individual falls on an outstretched hand. In young adults, fracture is the result of moderate to severe force. The risk of injury is increased in patients with osteoporosis and other metabolic bone diseases. In addition, when a fracture of the wrist occurs, the fracture may cause the radius to become short compared to the ulna. The ulna may then get caught when the wrist moves causing pain and restriction of movement.

The presently disclosed embodiments and methods treat a wrist fracture in a minimally invasive manner and can be used for a wrist reduction of any of the bones of the wrist and hands, in particular the radius and ulna.

The presently disclosed embodiments can be used to treat a clavicle fracture, resulting in a clavicle reduction. The clavicle or collar bone is classified as a long bone that makes up part of the shoulder girdle (pectoral girdle). Present methods to affix a broken clavicle are limited. The clavicle is located just below the surface of the skin, so the potential for external fixation including plates and screws is limited. In addition, the lung and the subclavian artery reside below the collar bone so using screws is not an attractive option. Traditional treatment of clavicle fractures is to align the broken bone by putting it in place, provide a sling for the arm and shoulder and pain relief, and to allow the bone to heal itself, monitoring progress with X-rays every week or few weeks. There is no fixation, and the bone segments rejoin as callous formation and bone growth bring the fractured bone segments together. During healing there is much motion at the fracture union because there is not solid union and the callous formation often forms a discontinuity at the fracture site. A discontinuity in the collar bone shape often results from a clavicle fracture.

The presently disclosed embodiments and methods treat a clavicle fracture in a minimally invasive manner and can be used for a clavicle reduction or collar bone reduction. A benefit of using a catheter to repair a collar bone is the repair minimizes post repair misalignment of collar bone. A benefit of using the catheter to repair a clavicle is to resolve the patient's pain during the healing process.

The devices and methods described herein may be used for a variety of applications, for example, they may be used to provide temporary support to an external splint or to form a plate.

Those skilled in the art will recognize that the disclosed apparatus and methods can be used for delivering reinforcing materials to other bones, such as radius, ulna, clavicle, metacarpals, phalanx, metatarsals, phalanges, tibia, fibula, humerus, spine, ribs, vertebrae, and other bones and still be within the scope and spirit of the disclosed embodiments.

In an embodiment, light is delivered to a first end of the bone void through a first catheter and glue is delivered to the other end (e.g., the second end) of the bone void through a second catheter. In an embodiment, both light and glue are delivered to the same end of the balloon and through separate catheters. In an embodiment, light and glue are delivered to the middle of the bone void through a single catheter. Light and glue may be delivered to the bone void through a single catheter or separate catheters, may be delivered to any location in the bone void (e.g., either end, middle or anywhere therebetween) and may be delivered to the same or different locations as one another, as not all of the present embodiments are intended to be limited in these respects.

In an embodiment, a sound may be used to clear the cavity of the bone of any extraneous material to ensure a conforming fit between the reinforcing material and the cavity, knocking off spicules. In an embodiment, a stent could be attached to the sound and is inserted through the cavity. The stent would remain within the cavity to support the cavity. The balloon would then be placed into the cavity after the stent has already been placed there. In an embodiment, a radial structural member may be located inside a balloon.

Advantages in treating osteoporotic bone and pathological fractures may include minimal entry points which will reduce soft tissue injury and subsequent adhesions and scar formation, benefits of adhesion, ability to apply variable Durometer materials within the lumen capable of changing the characteristics of the epoxies to meet the needs and challenges of the application, high tack and softer materials on the outside of the lumen for bonding with the bone and "shock absorption" on the outer layers and greater strength and rigidity on the inside.

Another advantage of using some of the presently disclosed embodiments may be that there is minimal soft tissue damage that occurs. Soft tissue damage creates callous formations which are considered part of the natural bone healing process. By minimizing the soft tissue damage, subsequent stiffness due to callous formations in and on the tendon is avoided. A small incision is made, through which the pin is driven into the cavity of the bone resulting in good approximation and fixation while there is no need for a cast that is required with traditional k-wire approach. The above identified advantages may result from some of the presently disclosed embodiments and not all embodiments necessarily have these advantages.

U.S. application Ser. No. 11/789,907, entitled "Apparatus and Methods for Delivery of Reinforcing Materials to Bone," filed Apr. 26, 2007, is hereby incorporated herein by reference in its entirety.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An apparatus for delivering a bone reinforcing mixture to a bone comprising:
    a tube having a proximal end, a distal end, and a longitudinal axis therebetween,
    wherein the tube has at least one inner lumen capable of allowing a bone reinforcing mixture to pass through; and
    a bone fitting portion having an opening for extending the tube through, a screw-thread portion for screwing through layers of the bone, a stopper that limits the insertion of the bone fitting portion into the bone, a grip portion for assisting in inserting the bone fitting portion into the bone, and at least one valve for relieving a pressure buildup in the bone void during delivery of the bone reinforcing mixture,
    wherein the screw-thread portion extends into a bone void of the bone, and
    wherein the tube extends through the bone fitting portion and into the bone.

2. The apparatus of claim 1 wherein the tube moves within the bone to reach different locations.

3. The apparatus of claim 1 wherein the bone reinforcing mixture has a viscosity of less than about 1000 cP.

4. The apparatus of claim 1 further comprising an adhesive system releasably attached at the proximal end of the tube for delivering the bone reinforcing mixture.

5. The apparatus of claim 4 wherein the adhesive system delivers a drug.

6. The apparatus of claim 1 wherein the screw-thread portion extends through an outer surface of the bone, through an inner surface of the bone, and into the bone void of the bone.

7. The apparatus of claim 1 wherein the distal end of the tube includes at least one fenestration.

8. A system for reinforcing a bone comprising:
    a tube having a proximal end, a distal end, and a longitudinal axis therebetween, wherein the tube has at least one inner lumen for allowing a bone reinforcing mixture to pass therethrough and a second inner lumen;
    a bone fitting portion having an opening for extending the tube through and a screw-thread portion for screwing through layers of the bone;
    an adhesive system engaging the proximal end of the tube for housing the bone reinforcing mixture; and
    a light source to provide light passing through the second inner lumen to harden the bone reinforcing mixture.

9. The system of claim 8 wherein the tube moves within a bone void of the bone to reach different locations within the bone void.

10. The system of claim 8 wherein the bone reinforcing mixture has a viscosity of less than about 1000 cP.

11. The system of claim 8 wherein the distal end of the tube includes a balloon portion capable of inflating and deflating.

12. The system of claim 8 wherein the bone fitting portion further comprises:
    a stopper that limits the insertion of the bone fitting portion into the bone,
    a grip portion for assisting in inserting the bone fitting portion into the bone, and
    at least one valve for relieving a pressure buildup in a bone void of the bone during delivery of the bone reinforcing mixture.

13. The system of claim 8 wherein the screw-thread portion extends through an outer surface of the bone, through an inner surface of the bone, and into a bone void of the bone, and wherein the tube extends through the bone fitting portion and into the bone.

14. The system of claim 8 wherein the adhesive system delivers a drug.

15. The system of claim 8 wherein the distal end of the tube includes at least one fenestration.

16. A method for reinforcing a bone comprising:
    penetrating the bone at a site adjacent to a weakened or fractured area of the bone to gain access to an interior of the bone;
    forming a bone void in the interior of the bone having a distal edge and a proximal edge;
    inserting a bone fitting portion at the penetration site, the bone fitting portion having an opening, a screw-thread portion for screwing through layers of the bone, and at least one relief valve;
    positioning a catheter having a proximal end, a distal end, and a longitudinal axis therebetween through the opening of the bone fitting portion so the distal end of the catheter is within the bone void;
    infusing a bone reinforcing mixture through at least one inner lumen of the catheter into the bone void; and
    removing the catheter from the bone fitting portion.

17. The method of claim 16 further comprising removing medullary material located in a medullary cavity of the bone to form the bone void.

18. The method of claim 16 further comprising moving the catheter towards the proximal edge of the bone void and infusing the bone reinforcing mixture through the catheter.

19. The method of claim 16 further comprising moving the catheter towards the distal edge of the bone void and infusing the bone reinforcing mixture through the catheter.

20. The method of claim 16 further comprising adding the bone reinforcing mixture until the bone reinforcing mixture has filled the bone void.

21. The method of claim 16 further comprising inserting reinforcing materials into the bone void before positioning the catheter through the opening, the reinforcing materials providing structure and support for the bone reinforcing mixture.

22. The method of claim 16 further comprising allowing the bone reinforcing mixture to harden and removing the bone fitting portion from the bone.

23. The method of claim 16 further comprising inserting an optical rod into a central space of the bone void and illuminating the rod to harden any remaining bone reinforcing mixture.

24. The method of claim 16 further comprising applying pressure to ensure that the bone reinforcing mixture fills the bone void.

* * * * *